(12) United States Patent
Garcia-Bengochea

(10) Patent No.: US 10,485,678 B2
(45) Date of Patent: Nov. 26, 2019

(54) INSTRUMENTS AND METHODS FOR ORTHOPEDIC IMPLANT ASSEMBLY

(71) Applicant: Javier Garcia-Bengochea, Jacksonville, FL (US)

(72) Inventor: Javier Garcia-Bengochea, Jacksonville, FL (US)

(73) Assignee: Javier Garcia-Bengochea, Jacksonville, FL (US)

( * ) Notice: Subject to any disclaimer, the term of this patent is extended or adjusted under 35 U.S.C. 154(b) by 0 days.

(21) Appl. No.: 15/985,534

(22) Filed: May 21, 2018

(65) Prior Publication Data

US 2018/0344481 A1 Dec. 6, 2018

Related U.S. Application Data

(63) Continuation-in-part of application No. 15/285,360, filed on Oct. 4, 2016, now Pat. No. 9,999,519.

(51) Int. Cl.
| | |
|---|---|
| *A61B 17/56* | (2006.01) |
| *A61F 2/44* | (2006.01) |
| *A61F 2/46* | (2006.01) |
| *A61B 17/02* | (2006.01) |

(52) U.S. Cl.
CPC .......... *A61F 2/4611* (2013.01); *A61B 17/025* (2013.01); *A61B 2017/0256* (2013.01); *A61F 2/447* (2013.01); *A61F 2002/4623* (2013.01)

(58) Field of Classification Search
CPC .............. A61B 17/0206; A61B 17/025; A61B 17/0218; A61B 17/02; A61B 17/34; A61B 17/3417; A61B 17/3468; A61B 17/1767; A61B 2017/0256; A61B 2017/0092; A61B 2017/3488; A61B 2090/062; A61B 2090/3966; A61F 2/4684; A61F 2/4611; A61F 2/447; A61F 2/4455; A61F 2002/302; A61G 13/1285
USPC ........................ 606/86 A, 99, 246, 264, 914; 623/17.11–17.16
See application file for complete search history.

(56) References Cited

U.S. PATENT DOCUMENTS

| | | | |
|---|---|---|---|
| 2,632,217 A | 3/1953 | Flora | |
| 5,967,973 A | 10/1999 | Sherts et al. | |
| 6,162,170 A | 12/2000 | Foly et al. | |
| 6,575,899 B1 * | 6/2003 | Foley | A61B 1/00105 600/102 |
| 6,929,606 B2 * | 8/2005 | Ritland | A61B 17/1757 600/201 |
| 7,774,905 B2 | 8/2010 | Geiger | |
| 8,016,829 B2 * | 9/2011 | Mahoney | A61B 17/025 606/86 A |
| 8,425,602 B2 * | 4/2013 | Guyer | A61B 17/02 606/86 A |
| 2008/0200767 A1 | 8/2008 | Ewers et al. | |

* cited by examiner

*Primary Examiner* — Pedro Philogene
(74) *Attorney, Agent, or Firm* — McNees Wallace & Nurick LLP

(57) ABSTRACT

A system for performing spinal surgery includes an assembly of one or more manipulation instruments for manipulating and positionally adjusting one or more implants within a spinal disc space. The assembly has a one or more of grasping and manipulating features with actuators and includes a shim instrument that has a body with at a wedge shaped spacer shim at its distal end and in an inverted orientation.

19 Claims, 21 Drawing Sheets

A

B

INSTRUMENTS AND METHODS FOR ORTHOPEDIC IMPLANT ASSEMBLY

RELATED APPLICATION

This application is a continuation-in-part of and claims the benefit of priority to U.S. patent application Ser. No. 15/285,360 filed Oct. 4, 2016, the entirety of which is incorporated herein by reference.

FIELD

The present application describes various exemplary instruments, systems and surgical techniques for achieving access to and placement of implants at a site within the body, particularly the spine. More particularly, the present application describes instruments and a system useful for accessing the spine for one or more purposes of placement, in situ assembly, and manipulation of intervertebral implants to supplement or replace natural spinal discs, particularly in the lumbar spine. The instruments are particularly useful for manipulation and controlled positioning of implants within the intervertebral space so as to enable arrangement and/or assembly to achieve desired distribution of implants across the surface of the vertebral endplates, and in some aspects to avoid expulsion thereof through any of the anterior, posterior and contralateral or ipsilateral annulus portions.

DESCRIPTION OF THE RELATED ART

Surgical access to the spine is achieved by a variety of different access routes, some or all of which involve complications and drawbacks depending on the condition of the patient, the extent of the disease or dysfunction, and the skill of the surgeon, among other factors. Access via anterior and posterior routes have certain advantages, but they are not necessarily minimally invasive, and involve some meaningful disadvantages, including the need for multiple surgeons (in the case of anterior access) and the need for creation of multiple openings into the disc space and related dura and soft tissue disruption (in the case of posterior access), among others.

Surgeons have evolved other modes of access, particularly for the lumbar spine, for example, through foramen of the spine (referred to as transforaminal lumbar interbody fusion, or TLIF). This mode of access involves unilateral entry into the disc space from a generally posterior approach that is affected by removing part or all of a single facet joint on one side of the spine to form a channel into the intervertebral space. This approach does not require dura retraction, it is not bilateral, it avoids muscle and soft tissue damage, and can be completed by a single surgeon.

Despite the described advantages to TLIF, there are drawbacks. For example, the channel through the resected facet is small, and presents only limited space for insertion of instruments and implants. This translates to what can be significant difficulty implant manipulation once an interbody device is placed in the disc space, and because of the limited space for insertion of instruments for achieving tissue distraction, it is also difficult to move an implant to enable placement of one or more additional implants. And, because the implants are relatively small, and thus cover a relatively small fraction of the surfaces of the endplates, there is a fairly high risk of failure as a result of collapse of the endplates around the implant. Thus, it is desirable to provide a system to enable the placement and positional manipulation of multiple implants and or to assemble an implant in situ. Such a system would permit desirable distribution of an implant or implant assembly across the disc space, and achieve better support between the vertebrae and resultant more stable fusion, while taking advantage of the minimally invasive aspects of TLIF and related spinal access approaches.

SUMMARY

In accordance with the disclosure, instruments and a surgical instrument system are provided, the instruments and system adapted for serially inserting and manipulating the position of implants within the disc space to enable sequential addition of two or more implants during a surgical procedure, particularly a spinal surgery, and more particularly a spinal surgery selected from posterior and transforaminal interbody fusion surgery. The instrument system permits controlled manipulation of an initially inserted implant within the disc space to allow for insertion of at least one additional implant adjacent the initial implant. According to some embodiments, the instruments are delivered (or otherwise actuated sequentially) in the disc space after insertion of at least a first implant (interbody device). In some embodiments, the system is adapted for assembling an implant in situ in the disc space, the implant assembled from one or a combination of sub components of implants, and from conventional implants that are positioned within the disc space and oriented relative to each other to achieve an implant assembly.

In various embodiments, the system includes a distractor blade instrument that is sized for insertion into the disc space and to distract the space between the vertebral endplates (from superior to inferior) and thereby stabilize the insertion space between the endplates for ease of movement of one or more implants. In some embodiments, the distractor blade instrument is stabilized or buttressed by a retractor tube or other retractor feature adjacent to the spine, to prevent lateral (sideways) movement of the instrument system within the disc space. The system may in some embodiments include a spacer shim instrument that is engageable with the distractor blade instrument and shaped to operate as a cam or linear cam which, when contacted with an implant, pushes and directs the implant in a sideways and/or rotational motion away from the initial insertion location and medially (toward the center) of the disc space. The system also includes in some embodiments an implant advancer instrument engageable with one or both of the distractor blade instrument and the spacer shim instrument, the implant advancer instrument adapted to be actuated at its proximal end to effect movement at its distal end into contact with an implant to achieve further sideways and/or rotational urging of one or more implants into the disc space.

In some embodiments the system includes a distractor blade instrument and a spacer shim instrument that cooperate together to achieve displacement of one or more implants positioned in the disc space. According to some such embodiments, the system also includes an implant advancer instrument.

In accordance with some embodiments, the instrument system is selected from arrays of one or more each of the distractor blade instrument, spacer shim instrument and implant advancer instrument, any one or more of which is provided in arrays having varying dimensional aspects, including size and shape of the distal shim portion of the spacer shim instrument, width and length and contour of the distal blade of the distractor blade instrument, and shape and length of the implant advancer instrument, the features selected to accommodate varying dimensions of access channels and for controlling direction and extent of movement of interbody devices within the disc space.

Also in accordance with the disclosure is a surgical technique for performing a procedure on the spine of a patient utilizing the surgical instruments and system hereof to enable controlled and reliable delivery of two or more implants into the intervertebral space without expulsion and along a substantially sideways (generally lateral to medial in the case of TLIF) path of travel between the end plates.

Embodiments of the present invention are not limited to use in a posterior or transforaminal approach for spinal surgery, and may be adapted for uses in other spinal surgical orientations and other surgical sites within the body.

BRIEF DESCRIPTION OF THE DRAWINGS

Features and advantages of the general inventive concepts will become apparent from the following description made with reference to the accompanying drawings, including drawings represented herein in the attached set of figures, of which the following is a brief description:

FIG. 21 B shows a front view of the embodiment of a distal shim of a spacer shim instrument shown in FIG. 21 A;

FIG. 21 C shows a side view of the embodiment of a distal shim of a spacer shim instrument shown in FIG. 21 A.

FIG. 22 B shows a front view of the embodiment of a distal shim of a spacer shim instrument shown in FIG. 22 A;

FIG. 22 C shows a side view of the embodiment of a distal shim of a spacer shim instrument shown in FIG. 22 A.

Figure 1:
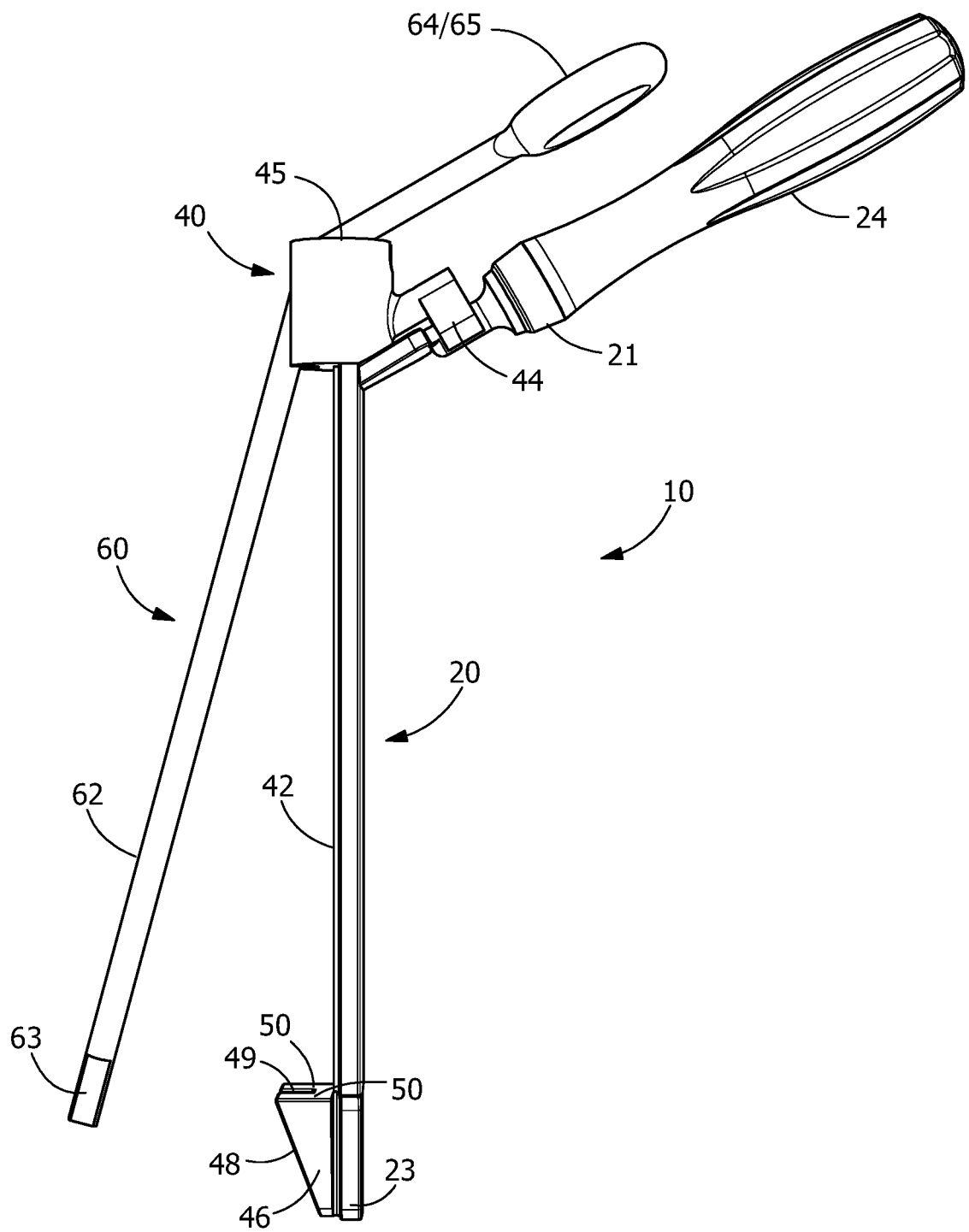
FIG. 1 shows an image of a representative embodiment of an implant positioner system including a distractor blade instrument, a spacer shim instrument, and an implant advancer instrument.

| Referenced Features | |
|---|---|
| surgical instrument assemblies | 10 |
| distractor blade instrument | 20 |
| Proximal end | 21 |
| body | 22 |
| distal blade | 23 |
| handle | 24 |
| proximal attachment feature | 25 |
| seat | 26 |
| cylindrical neck | 27 |
| spacer shim instrument carriage | 28 |
| stop feature | 29 |
| width dimension | 30 |
| Length dimension | 31 |
| Thickness dimension | 32 |
| Front side | 33 |
| Back side | 34 |
| Lateral edge | 35 |
| Distal edge | 36 |
| Corner | 37 |
| spacer shim instrument | 40 |
| Proximal portion | 41 |
| body | 42 |
| distal shim portion | 43 |
| clip | 44 |
| strike plate | 45 |
| wedge shaped | 46 |
| distal tip | 47 |
| substantially flat face | 48 |
| open receiving channel | 49 |
| proximal shoulders | 50 |
| Proximal base | 51 |
| Proximal base face | 52 |
| Opposing proximal base edges | 53 |
| Distal wedge portion | 54 |
| wedge edges | 55 |
| Wedge Back face | 56 |
| Distal extension | 57 |
| Distal edge | 58 |
| Distal extension face | 59 |
| implant advancer instrument | 60 |
| Proximal end | 61 |
| Body | 62 |
| Distal persuader element | 63 |
| actuator | 64 |
| pusher grip | 65 |
| tissue retractor tube | 80 |
| slots | 81 |
| clip with tabs | 82 |
| implant | 100 |
| Implant assembly | 110 |
| drawn representation of an intervertebral space | 120 |

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DESCRIPTION

The general inventive concepts will now be described with occasional reference to the exemplary embodiments of the invention. The general inventive concepts may be embodied in different forms and should not be construed as limited to the embodiments set forth herein. Rather, these embodiments are provided so that this disclosure will be thorough and complete, and will fully convey the scope of the general inventive concepts to those skilled in the art.

As used herein, the singular forms "a," "an," and "the" are intended to include the plural forms as well, unless the context clearly indicates otherwise. The term "proximal" as used in connection with any object refers to the portion of the object that is closest to the operator of the object (or some other stated reference point), and the term "distal" refers to the portion of the object that is farthest from the operator of the object (or some other stated reference point). The term "operator" means and refers to any professional or paraprofessional who delivers clinical care to a medical patient, particularly in connection with the delivery of care.

Anatomical references as used herein are intended to have the standard meaning for such terms as understood in the medical community. For example, the application may include reference to the following terms: "cephalad," "cranial" and "superior" indicate a direction toward the head, and the terms "caudad" and "inferior" indicate a direction toward the feet. Likewise, the terms "dorsal" and "posterior" indicate a direction toward the back, and the terms "ventral" and "anterior" indicate a direction toward the front. And the term "lateral" indicates a direction toward a side of the patient. The term "medial" indicates a direction toward the mid line of the patient, and away from the side, the term "ipsilateral" indicates a direction toward a side that is proximal to the operator or the object being referenced, and the term "contralateral" indicates a direction toward a side that is distal to the operator or the object being referenced. And, more specifically with respect to the directional movement of an implant according to the methods of the disclosure, sideways refers to the general direction of movement within the disc space between the endplates from the position of the inserted instruments toward one or the other of the contralateral and ipsilateral portions of the disc space. In the case of a TLIF procedure, such sideways motion will generally be in a medial direction relative to the disc space. Though in other types of surgical access, particularly within the spine, sideways movement may be either medial or lateral relative to the disc space, and in other surgical contexts sideways is away from the initial position of the implant. Further, with respect to the movement of an implant by action of the surgical instruments, the movement may also be rotational, wherein the action of the instruments directs the implant sideways and also in a rotational or pivotal motion. More generally, any and all terms providing spatial references to anatomical features shall have meaning that is customary in the art.

Unless otherwise indicated, all numbers expressing quantities, properties, and so forth as used in the specification, drawings and claims are to be understood as being modified in all instances by the term "about." Accordingly, unless otherwise indicated, the numerical properties set forth in the specification and claims are approximations that may vary depending on the suitable properties desired in embodiments of the present invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

References to visualization using radiography as may be described in the exemplary techniques herein are merely representative of the options for the operator to visualize the surgical field and the patient in one of many available modalities. It will be understood by one of ordinary skill in the art that alternate devices and alternate modalities of visualization may be employed depending on the availability in the operating room, the preferences of the operator and other factors relating to exposure limits. While confirmation of instrument placement in the course of the technique is appropriate, the frequency and timing relative to the sequence of steps in the technique may be varied and the description herein is not intended to be limiting. Accordingly, more or fewer images, from more or fewer perspectives, may be collected.

One of ordinary skill will appreciate that references to positions in the body are merely representative for a particular surgical approach. Further, all references herein are made in the context of the representative images shown in the drawings. Fewer or additional instruments, including generic instruments, may be used according to the preference of the operator. Moreover, references herein to specific instruments are not intended to be limiting in terms of the options for use of other instruments where generic options are available, or according to the preference of the operator.

There is a need for devices and systems that overcome the shortcomings in the art pertaining to placement of more than a single implant in the context of minimally invasive surgery, particularly spinal surgery, and more particularly access via a transforaminal or TLIF procedure. In view of this need, the embodiments of devices, systems, and surgical methods provided herein address a variety of objects and advantages. The present application describes various exemplary devices, systems and surgical methods for achieving placement of multiple interbody devices in the space between two vertebrae. More particularly, the present application describes instruments for manipulating and placing multiple implants in a disc space while maintaining modest distraction suitable to enable smooth movement of implants into desired position within the disc space prior to removal of the instruments.

Surgical Instrument Assemblies

In accordance with various embodiments, provided herein are surgical instrument assemblies 10. Referring now to the drawings, FIG. 1 shows an image of a representative embodiment of an implant positioner system including a distractor blade instrument 20, a spacer shim instrument 40, and an implant advancer instrument 60 in a first configuration, and in FIG. 2 in a second configuration, and in FIG. 3 the instruments of the system are shown disassembled. The system includes a distractor blade instrument 20 (also referred to as an endplate distractor) that is sized for insertion to distract the disc space (from superior to inferior) and/or stabilize the insertion space between the endplates for relative ease of movement of one or more implants or implant assembly components. The system also includes a spacer shim instrument 40 that is engageable with the distractor blade instrument 20 and shaped to operate as a cam or linear cam which when contacted with the implant pushes and directs the implant in a sideways and/or rotational motion away from the initial insertion location. The system also includes an implant advancer instrument 60 engageable with one or both of the distractor blade instruments 20 and the spacer shim instrument 40, the implant advancer instrument 60 adapted to be actuated at its proximal end 61 to effect movement at its distal end into contact with an implant to achieve further sideways and/or rotational urging of one or more implants into the disc space.

In accordance with some embodiments, it is contemplated that each of the blade, spacer shim instrument 40 and implant advancer instrument 60 components are used to one or more of insert, move or reposition one or more implant or implant components. In some embodiments only one of the instruments may be used. For example, in some embodiments the distractor blade instrument 20 may be used to support and guide insertion of one or a series of implants without use of either the spacer shim instrument 40 or the implant advancer instrument 60. In yet other embodiments, only the spacer shim instrument 40 may be used to advance movement of an implant to enable insertion of one or more additional implants. And in yet other embodiments, the assembly may be limited to the distractor blade instrument 20 and spacer shim instrument 40 components without use of the implant advancer instrument 60.

Figure 2:
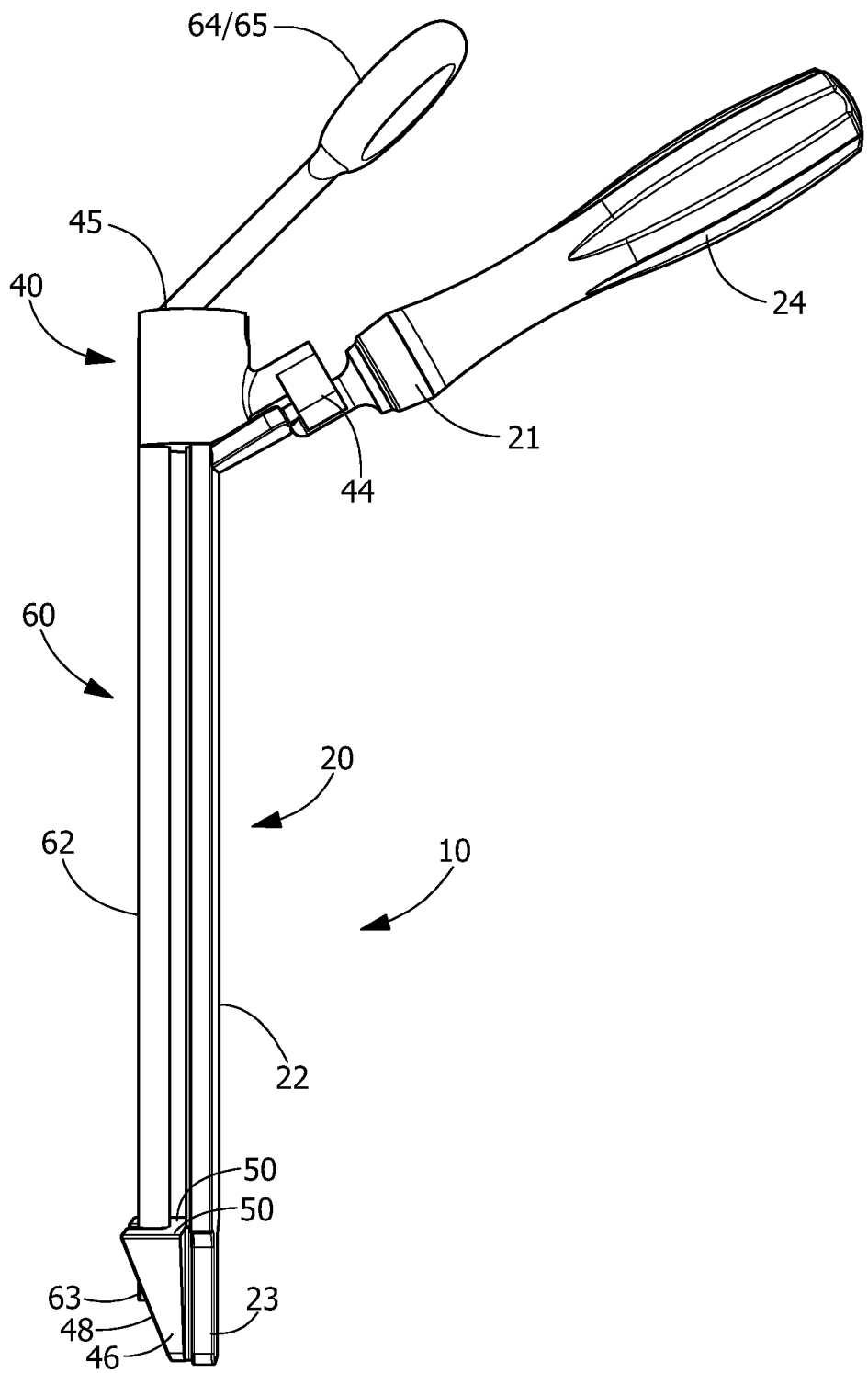
FIG. 2 shows an image in an alternate operational mode of the implant positioner system shown in FIG. 1.
Figure 3:
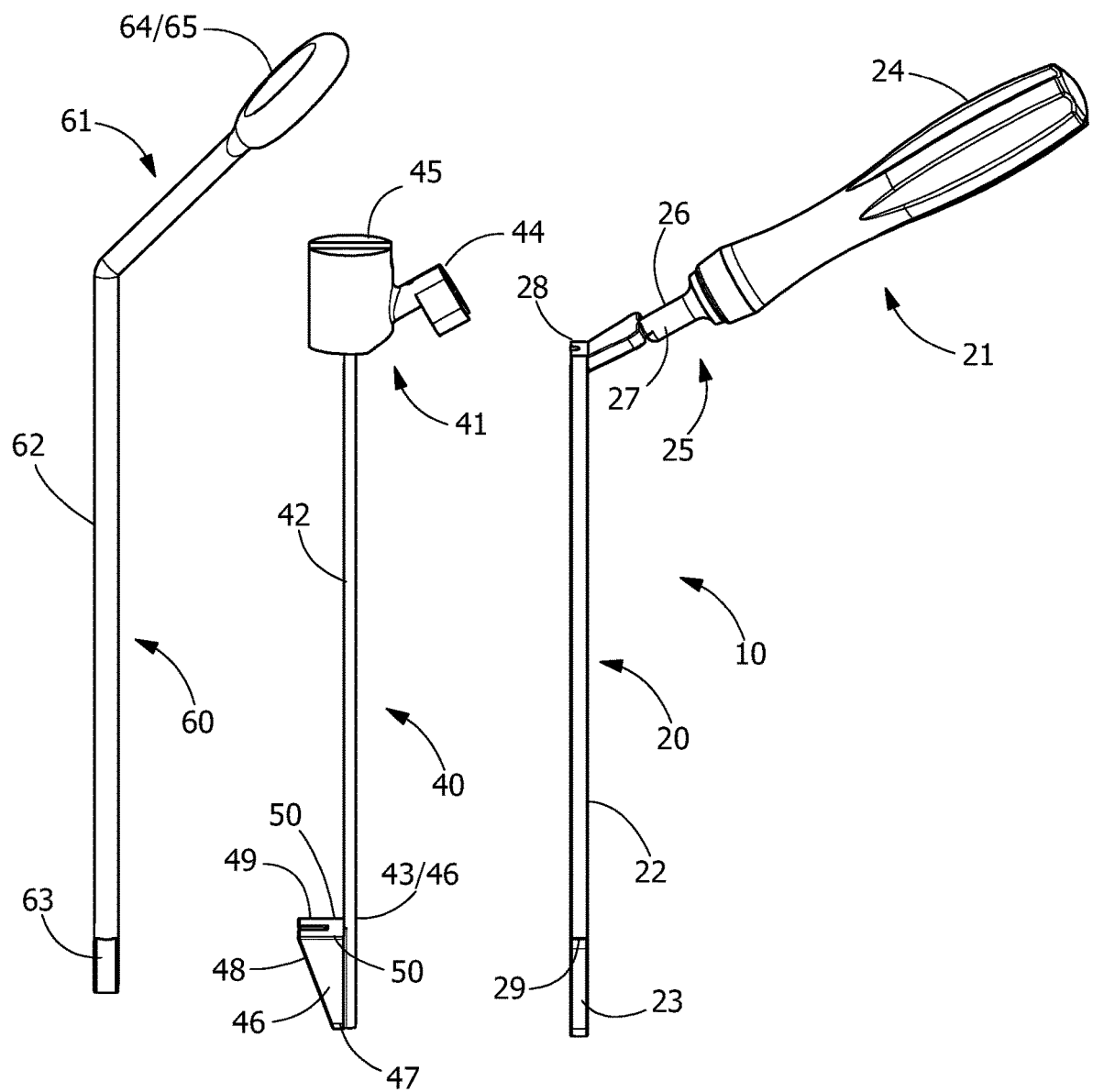
FIG. 3 shows an image of the components of the implant positioner system shown in FIG. 1.

Referring again to the drawings, FIG. 3 depicts an instrument system wherein the instruments are disassembled, in which side views of each of the instruments of the system embodiment from FIG. 1 and FIG. 2 are shown. In accordance with some embodiments, as depicted, the distractor blade instrument 20 (instrument shown on the right of the image) has a proximal end 21 with a handle 24 and a distal blade 23, and is adapted with a carriage 28 and having a stop feature 29, the carriage 28 along a length between the proximal end 21 and distal blade 23. The spacer shim instrument 40 (shown in the center of the image) is engageable with at least the spacer shim instrument carriage 28 of the distractor blade instrument 20 and has a distal shim portion 43 at its distal blade 23. And the implant advancer instrument 60 (shown on the left of the image) is engageable with one or both of the distractor blade instrument 20 and the spacer shim instrument 40, the implant advancer instrument 60 adapted with an actuator 64 at a proximal end 61. In accordance with some embodiments, each of the distractor blade instrument 20, the spacer shim instrument 40 and the implant advancer instrument 60 are elongate.

The system is adapted for inter-engagement of the instruments upon insertion within a prepared surgical space to manipulate the orientation of one or more implants therein and in some particular instances to enable sequential addition of two or more implants during a surgical procedure, particularly a spinal surgery, and more particularly a spinal surgery selected from posterior and transforaminal interbody fusion surgery. The system permits controlled manipulation of an initially inserted implant within the disc space so as to enable optimized positioning of the implant or one or more components of an implant assembly in the disc space. An additional benefit may include minimizing the risks of expulsion of an implant from the space. The system also allows for positional adjustment of a first implant within the space to permit subsequent insertion of at least one additional implant initially adjacent the initial implant. The instrument system thus allows the surgeon to place one or more implants within the disc space at positions that more closely match and accommodate the patient's anatomy taking into account bone condition as well as vertebral size. According to some embodiments, the instruments are delivered (or otherwise actuated sequentially) in the disc space after insertion of at least a first implant (interbody device).

Endplate Distractor Blade Instrument

Figure 4:
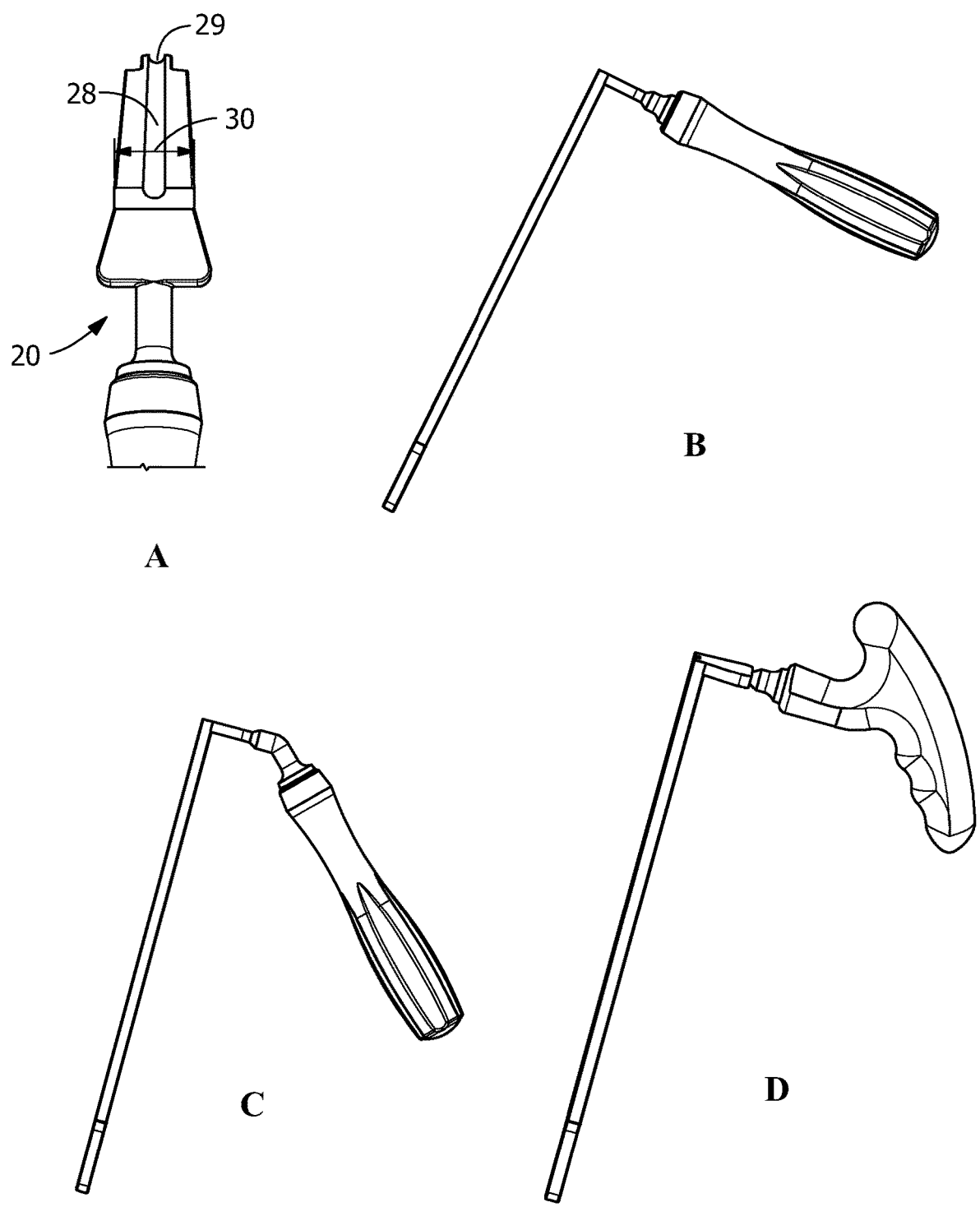
FIG. 4A shows a close-up view from the proximal portion of the distractor blade instrument along the length dimension.
FIG. 4B shows an embodiment of a distractor blade instrument of an implant positioner system in accordance with the disclosure, having a handle oriented at 90 degrees relative to the extended and distal portions of its shaft and spacer shim instrument carriage.
FIG. 4C shows an alternate embodiment of a distractor blade instrument of an implant positioner system in accordance with the disclosure, having a handle oriented at greater than 90 degrees relative to the extended and distal portions of its shaft and spacer shim instrument carriage.
FIG. 4D shows an alternate embodiment of a distractor blade instrument of an implant positioner system in accordance with the disclosure, having an alternate profile of a handle oriented at 90 degrees relative to the extended and distal portions of its shaft and spacer shim instrument carriage.

Referring again to the drawings, FIG. 4 shows alternate views of an embodiment of a distractor blade instrument 20 of a surgical instrument assembly 10 in accordance with the disclosure. The distractor blade instrument 20 has a proximal end 21 with a handle 24 and a distal blade 23, shown in three possible orientations in panels B, C and D, and adapted with an spacer shim instrument carriage 28 along a length between the proximal end 21 and distal blade 23. The endplate distractor blade instrument 20 functions in one aspect as a buttress against the wall of a tube or other retractor blade so that when the spacer shim instrument 40 is advanced into the disc space, the buttress effect will allow the implant to move medially and will prevent the distractor blade instrument 20 and spacer shim instrument 40 from being forced laterally (towards the ipsilateral or contralateral side) within the disc space by the implant as the spacer shim instrument 40 is advanced distally along the distractor blade instrument 20 into the disc space.

Of course, it will be appreciated that in other embodiments, stabilization or buttressing of the distractor blade instrument 20 may be achieved by its attachment or fixation to another instrument, or by placement of a stabilizing instrument either within the disc space or at a proximal position outside of the surgical field against which the distractor blade instrument 20 may be positioned to discourage movement of the instruments rather than movement of the implant. Thus, in the case of a TLIF procedure, for example, buttressing will prevent lateral movement of the implant manipulation instruments and thus encourage medial movement of the implant as the instruments are assembled in the disc space.

In accordance with various embodiments, the implant distractor blade instrument 20 may have any of a number of proximal end 21 handle 24 features, where in one example, FIG. 4 B shows an embodiment of the distractor blade instrument 20 with a handle 24 oriented at 90 degrees relative to the extended and distal portions of its shaft and spacer shim instrument carriage 28. Each of FIGS. 4 C and 4 D show alternate handle 24 orientations, including a handle 24 oriented at greater than 90 degrees relative to the extended and distal portions of its shaft and spacer shim instrument carriage 28, and a handle 24 oriented at 90 degrees relative to the extended and distal portions of its shaft and spacer shim instrument carriage 28.

Figure 5:
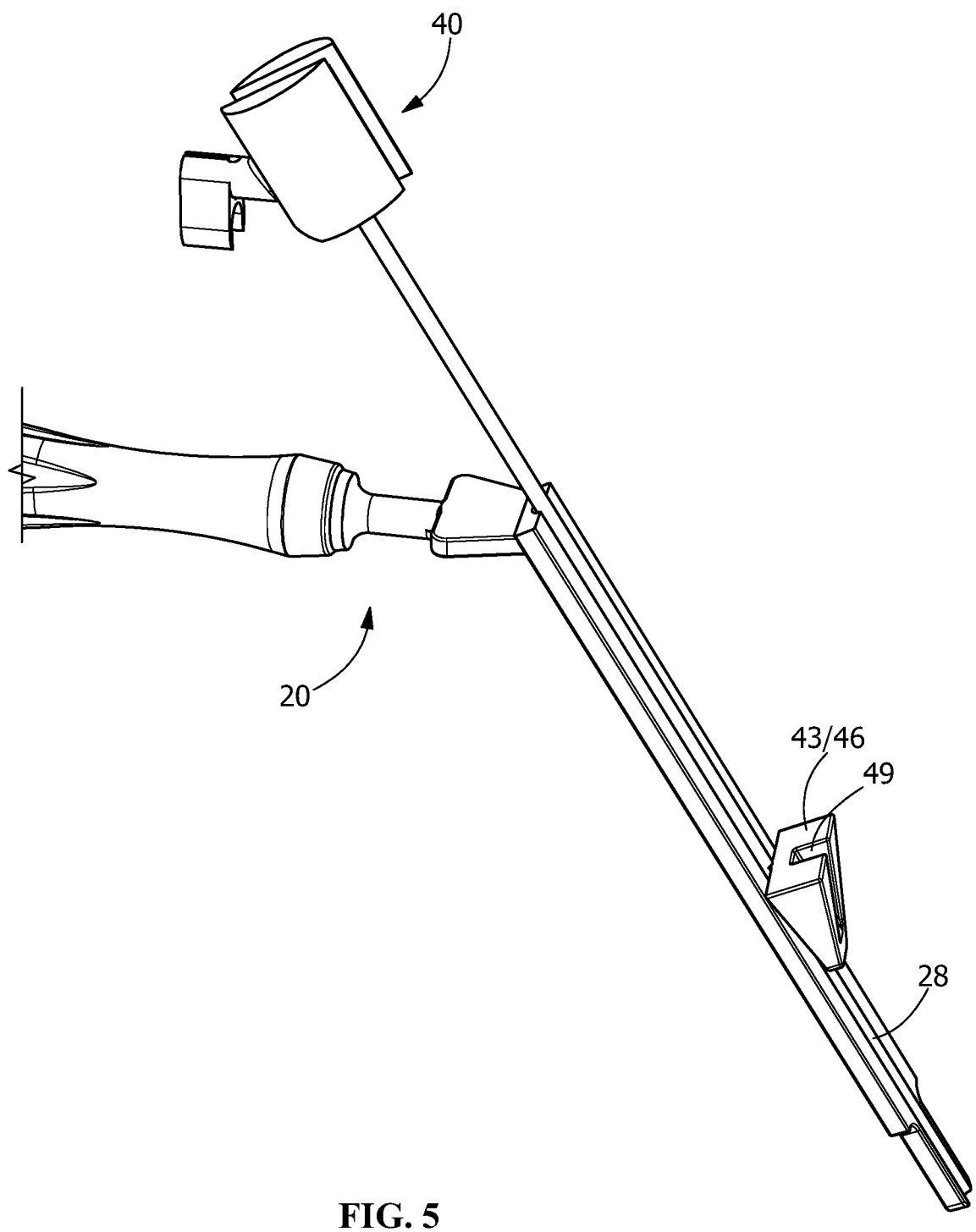
FIG. 5 shows an image of a sub assembly of the distractor blade instrument and spacer shim instrument components of an alternate embodiment of an implant positioner system according to the disclosure, the spacer shim instrument comprising a clip for fixed engagement with the distractor blade instrument, oriented prior to engagement of the clip with a proximal attachment feature of the distractor blade instrument.

Referring again to the drawings, FIG. 1 shows an image of the distractor blade instrument 20 partially engaged along its length with the spacer shim instrument 40 component of the implant positioner system shown in FIG. 1. In the depicted embodiment, the distractor blade instrument 20 is adapted with a seat 26 at its proximal end 21 for supporting a fully engaged spacer shim instrument 40. Referring now to FIG. 5, the sub assembly of the distractor blade instrument 20 and the spacer shim instrument 40 are shown from the proximal end 21 in a partially engaged configuration and in FIG. 6 in a fully engaged configuration, where in the depicted embodiment a clip 44 on the proximal portion 41 of the spacer shim instrument 40 is engaged with the proximal end 21 of the distractor blade instrument 20.

In accordance with some embodiments, the distractor blade instrument 20 has a width dimension 30 that is greater than a thickness dimension along at least a portion of its length between the proximal end 21 and distal blade 23. In accordance with some embodiments, the carriage 28 of the distractor blade instrument 20 comprises an elongate slot along at least a portion of its length between the proximal and distal ends and comprises at its distal end a stop feature 29 for halting distal advancement of a spacer shim instrument 40 engaged with the spacer shim instrument carriage 28. Of course, in other embodiments, the spacer shim instrument carriage 28 for engagement with the spacer shim instrument 40 may vary in one or more features, including but not limited to the shape of the engaged body and carriage features, the mode of engagement, and the travel of the carriage. Thus, in some embodiments, the carriage may be a rod, ridge or other positive feature that is engageable with a corresponding channel or slot on the spacer shim instrument 40. Likewise, the engagement features may have a cross sectional shape that is other than circular, and may be for example triangular, trapezoidal, hexagonal, noncircular elliptical or another shape.

In accordance with some embodiments, the distractor blade instrument 20 is adapted at its proximal end 21 for engagement with a fastener near the proximal end of the spacer shim instrument 40, and the spacer shim instrument 40 comprising near its proximal portion 41 a clip 44 for engagement with the distractor blade instrument 20 and a strike plate 45 for facilitating distally directed force along the length of the spacer shim instrument 40. In some embodiments, the adaptation at the proximal end 21 of the distractor blade instrument 20 includes a seat 26 for supporting the strike plate 45 of the spacer shim instrument 40 and a cylindrical neck 27 adjacent the strike plate 45 seat 26 for receiving the spacer shim instrument 40 clip 44. In other embodiments, the neck 27 may have another cross-sectional shape that is complimentary with the spacer shim clip 44, the shape selected from cylindrical, and non-cylindrical, including hemi-cylindrical, square, and hexagonal, and other polygonal shapes.

In some embodiments, there may be an array of distractor blade instruments 20 having varying thicknesses and widths, and having different sizes to enable selection for one or more of matching the size of the target disc space, matching the dimensions of a selection of implants, or for matching the size and shape of adjacent spacer shim instruments 40.

In the various embodiments, the distractor blade instrument 20 has a width dimension 30, a length dimension 31, a thickness dimension 32 between front and back sides 33, 34, lateral edges 35, and a contour of its distal blade 23 that is defined by each of the width dimension 30, length dimension 31, and thickness dimension 32, and the distal edge 36. As depicted in the drawings in some embodiments, the front side 33 of the distal blade 23 is adapted with the spacer shim instrument carriage 28, and is opposite the back side 34 of the distal blade 23. In the various embodiments, the width dimension 30 may be constant from proximal to distal along the body 22 of the distractor blade instrument 20, including the distal blade 23, or it may vary. Thus, in some embodiments, the distal blade 23 is wider as compared to the width of the proximal end of the body 22 of the distractor blade instrument 20. And in some embodiments, the distal blade 23 is narrower as compared to the width of the proximal end 21 of the body 22 of the distractor blade instrument 20, as shown in FIG. 5, and in FIG. 7A, where it is evident that the blade tapers from the body 22 approximately adjacent the proximal base of the distal shim portion 43. Also in the various embodiments, the thickness dimension 32 may be constant from proximal to distal or it may vary. Thus, in some embodiments, the distal blade 23 has a thickness that is greater as compared to the thickness of the body 22 at the proximal end 21 of the distractor blade instrument 20. And in some embodiments, the distal blade 23 has a thickness that is smaller as compared to the thickness of the body 22 at the proximal end 21 of the distractor blade instrument 20.

Further, in the various embodiments, the distal blade 23 has a contour that is defined by each of the width dimension 30, length dimension 31, and thickness dimension 32. In some embodiments, the contour is one of planar and shaped. Thus, in some embodiments, the distal blade 23 has a contour that is flat and planar in some embodiments, the distal blade 23 at its distal edge 36 being generally squared in one or both of its width dimension 30 and thickness dimensions 32, the contour along at least a portion of the length dimension 31 of the body 22. In some embodiments, the distal blade 23 has a shaped contour in at least one of its width and thickness dimensions 30, 32. In some such embodiments, the distal blade 23 is shaped and is either angled or radiused (curved) in one or more of its width dimension 30 and its thickness dimensions 32. Thus, in some embodiments, as shown for example in FIG. 1-FIG. 3, the distal blade 23 is angled at each corner 37 of its distal edge 36 to form a taper along the distal portion of its length dimension 31, where the width at the distal tip is narrow relative to the proximal portion 41 of the distal blade 23, and matches the angled shape of the distal tip of the distal shim portion 43, as shown in FIG. 3. In some embodiments, the contour of the distal blade 23 is shaped, and the distal blade 23 is tapered on one or both of front and back sides 33, 34 in its thickness dimension 32, the taper being one of angled and radiused. And in some particular embodiments, the contour of the distal blade 23 is shaped, and the distal blade 23 is tapered at each corner 37 of its width dimension 30 and along at least the distal portion of its length dimension 31, the taper being one of angled and radiused, where the width at the distal edge 36 is narrow relative to the proximal portion of the distal blade 23, and the distal blade 23 is tapered on one or both of front and back sides 33, 34 in its thickness dimension 32, the taper being one of angled and radiused. Thus, in some embodiments, the distal blade 23 has a contour that includes along a portion of its length at its distal end a taper in each of its thickness and width dimensions 32, 30, the taper being either angled or radiused (curved). And in some particular embodiments, the distal blade 23 has a back side 34 that has an angled taper to its thickness dimension 32 the taper originating on the back side 34 at a proximal position along the length dimension 31, and the distal blade 23 also has an angled taper to its width dimension 30, the taper originating on each of the lateral edges 35 at a proximal position along the length dimension 31, the distal blade 23 having a cross sectional shape that is generally trapezoidal. Further, in some embodiments the distal edge 36 along the width dimension 30 may be flat or radiused (curved) along all or a portion between the corners 37. In some particular embodiments, the distal edge 36 is radiused. More generally, in addition to and encompassing the embodiments of the distal blade 23 as described herein, the distal blade 23 may have along at least a portion of its length, including at its distal edge 36, a cross sectional shape selected from cylindrical, or non-cylindrical, including hemi-cylindrical, square, and hexagonal, and other polygonal shapes.

Spacer Shim

Figure 6:
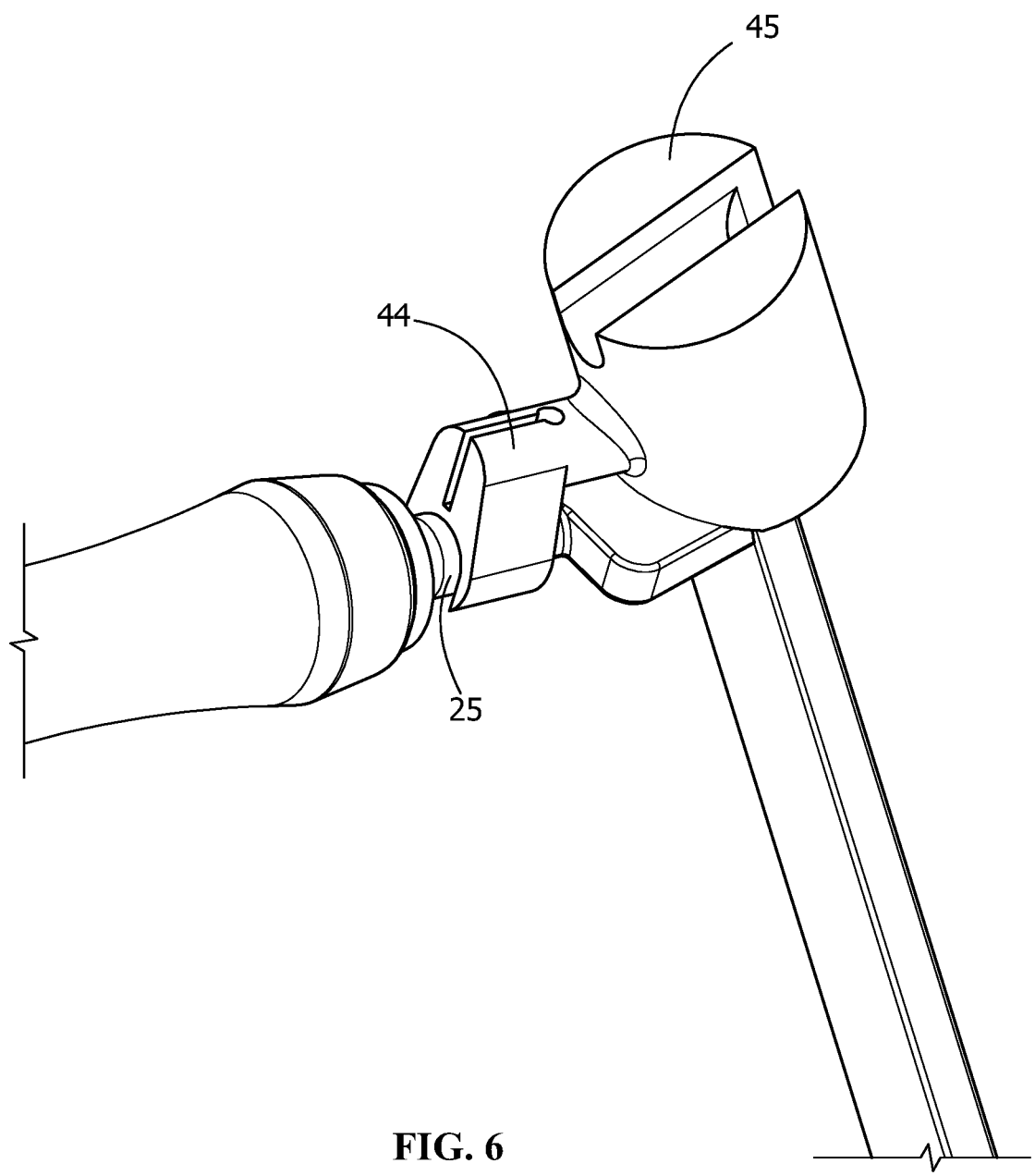
FIG. 6 shows an image of a sub assembly of the distractor blade instrument and spacer shim instrument components of an alternate embodiment of an implant positioner system according to the disclosure, the spacer shim instrument comprising a clip for fixed engagement with the distractor blade instrument, oriented in an engaged configuration between the spacer shim instrument clip and the proximal attachment feature of the distractor blade instrument.

Referring again to FIG. 1, the spacer shim instrument 40 (shown in the center of the image) is engageable with at least the engagement carriage of the distractor blade instrument 20 and has a distal shim portion 43 at its distal end. In some embodiments, as shown in the various drawings, the spacer shim instrument 40 has an elongate and generally cylindrical body 42 that is engageable within a channel formed as a spacer shim instrument carriage 28 on the distractor blade instrument 20. FIG. 5 and FIG. 6 each shows an image of a sub assembly of the distractor blade instrument 20 and spacer shim instrument 40 components of an alternate embodiment of an implant positioner system according to the disclosure, the spacer shim instrument 40 comprising a clip 44 for fixed engagement with the distractor blade instrument 20, oriented prior to engagement of the clip 44 with a proximal attachment feature 25 of the distractor blade instrument 20. In other embodiments, the body 42 may have another cross sectional shape that is selected from cylindrical, and non-cylindrical, including hemi-cylindrical, square, and hexagonal, and other polygonal shapes.

According to such embodiments, the distal shim portion 43 of the spacer shim instrument 40 is oriented on the body 42 so that the body 42 can engage with the distractor blade instrument 20 to a terminal point (stop feature) 29 where the tip of the spacer shim instrument 40 is aligned with the distal tip 47 of the distractor blade instrument 20. Of course, in other embodiments, the engagement of the spacer shim instrument 40 body 42 with the distractor blade instrument 20 may vary in one or more features, including but not limited to the shape of the engaged body 42 and spacer shim instrument carriage 28 features, the mode of engagement, and the travel of the spacer shim instrument carriage 28. Thus, in some embodiments, the spacer shim instrument 40 may have a distractor blade instrument 20 like shape with a channel and the distractor blade instrument 20 may comprise a rod or other elongate structure engageable therewith (i.e., an engagement configuration that is the opposite of that depicted in FIG. 1). Likewise, the engagement features may have a cross sectional shape that is other than circular, and may be for example triangular, trapezoidal, hexagonal, non-circular elliptical or another shape.

Figure 7:
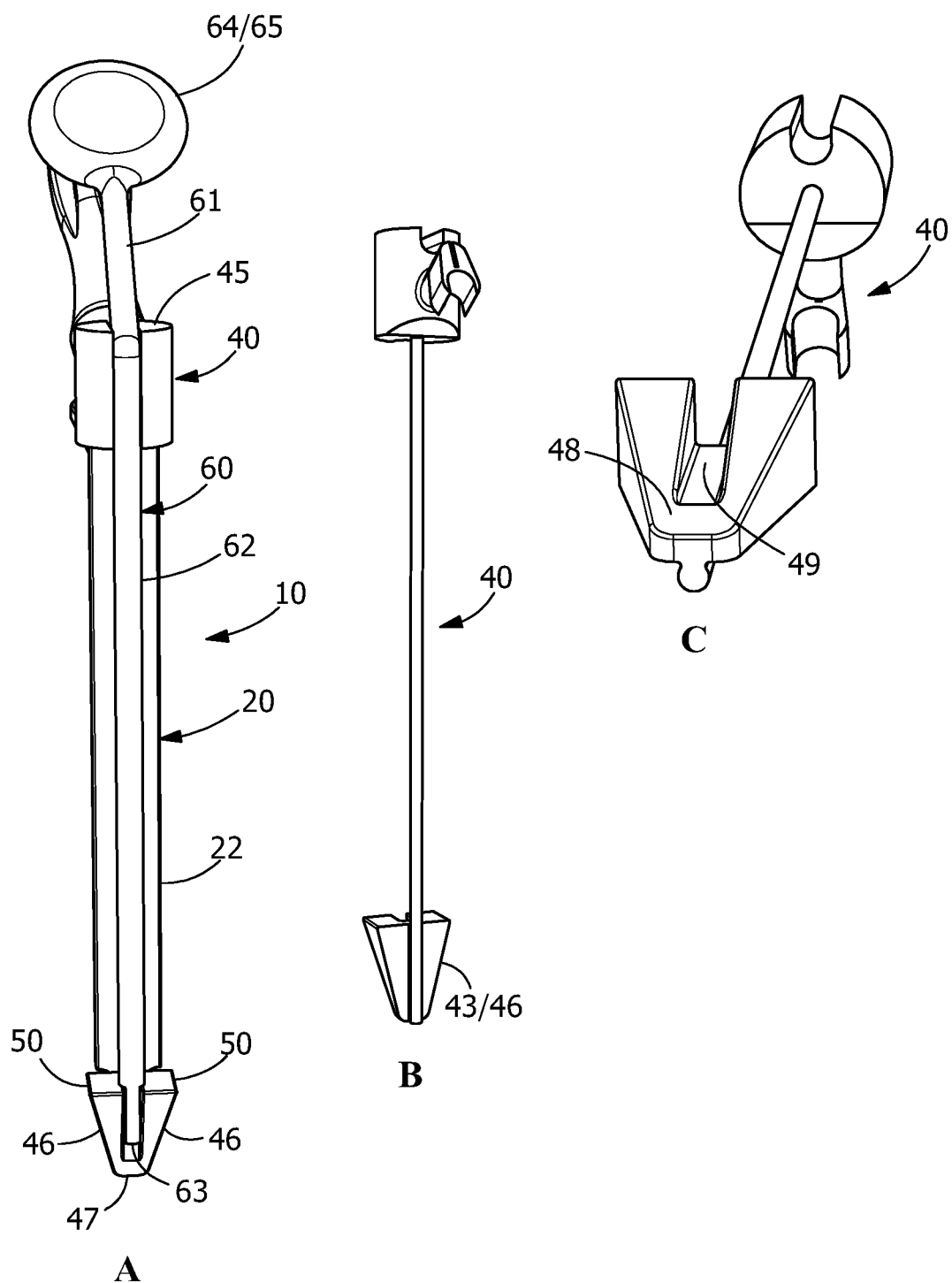
FIG. 7A shows an image of a sub assembly of the spacer shim instrument and implant advancer instrument components of the implant positioner system shown in FIG. 1.
FIG. 7B shows an image of the spacer shim instrument component of the implant positioner system shown in FIG. 1.
FIG. 7C shows a close-up view from the distal shim of the spacer shim instrument along the length dimension of the spacer shim instrument.

Referring again to the drawings, FIG. 7 B shows an image of the spacer shim instrument 40 component of the implant positioner system 10 shown in FIG. 1, in FIG. 7 A in the context of an engaged implant advancer instrument 60, and in FIG. 7 C a close-up view from the distal shim portion 43 of the spacer shim instrument 40 along the length dimension of the spacer shim instrument 40. According to the depicted embodiment of FIG. 7, the distal shim portion 43 includes a wedge shaped 46 spacer shim or linear cam that is angled at both the front and the sides to taper to a cone, having a generally cylindrical slot (open receiving channel) 49 that terminates near the conical distal tip 47 in a squared slot for receiving an implant advancer instrument 60, and having a striking plate 45 at the proximal portion 41. In other embodiments, the channel 49 may have another cross-sectional shape that is selected from cylindrical, and non-cylindrical, including hemi-cylindrical, square, and hexagonal, and other polygonal shapes. And in other embodiments, the channel 49 for receiving an implant advance may have a shape other than squared, and may thus have a cross sectional shape that is selected from cylindrical, and non-cylindrical, including hemi-cylindrical, hexagonal, and other polygonal shapes.

In accordance with some embodiments, the distal shim portion 43 at the distal end of the spacer shim instrument 40 is selected from a cam and a linear cam which when contacted with the implant advancer instrument 60 pushes and directs the implant advancer instrument 60 in a sideways and/or rotational motion away from the initial insertion location. In some particular embodiments, the spacer shim instrument 40 at the distal shim portion 43 of the spacer shim instrument 40 has a wedge shape 46 selected from conical, frusto trapezoidal, frusto conical, frusto pyramidal, and polygonal. In accordance with some embodiments, the wedge shaped 46 distal shim portion 43 is positioned on the distal end of the spacer shim instrument 40 in an inverted orientation with a proximal base 51 oriented proximally, a distal tip 47 oriented distally and comprising at least one substantially flat face 48 comprising an open receiving channel 49 within the substantially flat face 48, the receiving channel terminating at a point above the distal tip 47 of the wedge 46 and shaped to accommodate a distal portion of the implant advancer instrument 60. In some embodiments the spacer shim instrument 40 is not adapted to engage with any other instrument.

Figure 8:
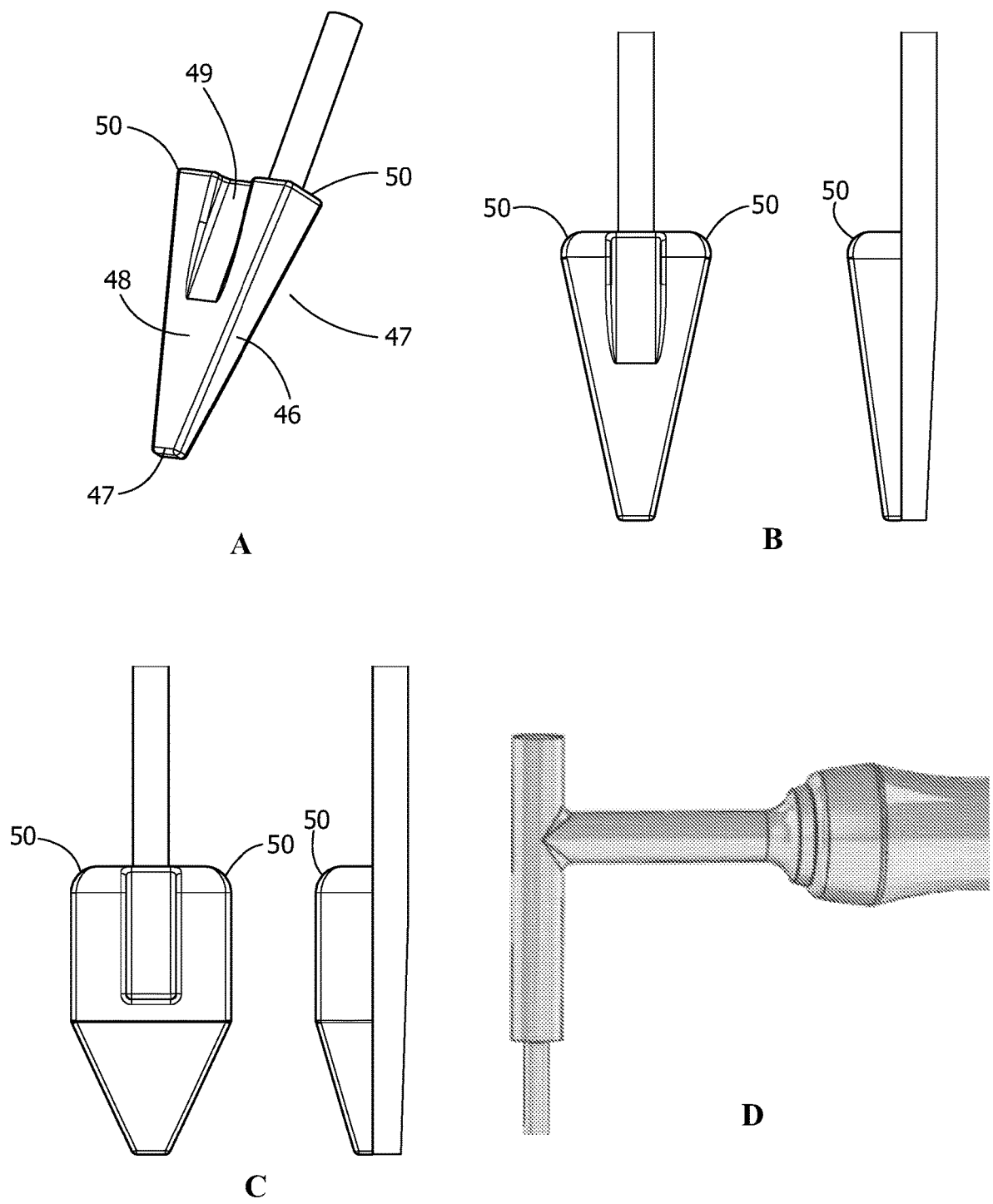
FIG. 8A shows a representative embodiment of a distal shim of a spacer shim instrument of the implant positioner system shown in FIG. 1.
FIG. 8B shows an alternate embodiment of a distal shim of a spacer shim instrument of the implant positioner system shown in FIG. 1.
FIG. 8C shows another embodiment of a distal shim of a spacer shim instrument of the implant positioner system shown in FIG. 1.
FIG. 8D shows a representative embodiment of a proximal portion of a spacer shim instrument of the implant positioner system shown in FIG. 1, where according to the depicted embodiment, the distal shim end includes a wedge shaped spacer shim instrument or linear cam that is angled at both the front and the sides to taper to a cone, having a generally cylindrical slot that terminates near the conical tip in a squared slot for receiving an implant advancer instrument, and having a striking surface at the proximal end.

Referring again to the drawings, FIG. 8 A shows a representative embodiment of a distal shim portion 43 of a spacer shim instrument 40, and FIG. 2 D shows a representative embodiment of a proximal portion 41 of a spacer shim instrument 40 of the surgical instrument assembly 10. In some embodiments such as shown in FIG. 8 A the spacer shim instrument 40 is generally triangular wedge shaped 46 with squared proximal shoulders 50 and tapering to a squared frusto-pyramid. As shown in alternate embodiments, as depicted in FIGS. 8 B and 8 C, the shape may be other than a triangular wedge, and the spacer shim instrument 40 may have rounded proximal shoulders 50. Referring again to FIG. 8, the depicted shim has a wedge shaped 46 with a distal tip 47, and its proximal base 51 is squared with a proximal base face 52 that is generally parallel to a long axis of the body 42 of the spacer shim instrument 40 and opposing proximal base edges 53, the proximal base face 52 and opposing proximal base edges 53 forming a block shape, the distal shim portion 43 including a distal wedge portion 54 that includes an substantially flat face 48 and opposing wedge edges 55 that taper along at least a portion of the length of the substantially flat face 48. The wedge shaped 46 as depicted in the embodiments as shown in FIG. 8 A-FIG. 8 C include a substantially flat wedge face 48 that is at an angle relative to the long axis of the spacer shim instrument 40 and a wedge back face 56 that is opposite the substantially flat wedge face 48 and is angled relative to the long axis of the spacer shim instrument 40 inward toward the substantially flat wedge face 48.

Figure 21:
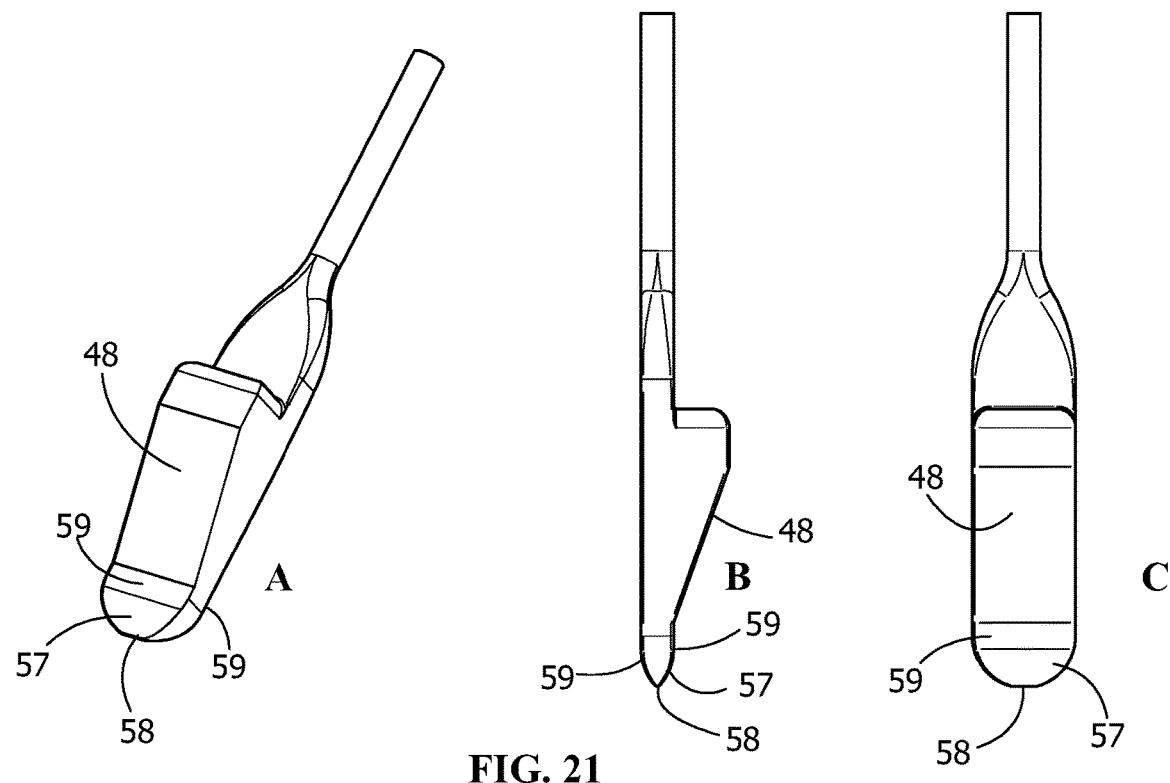
FIG. 21 A shows a front perspective view of an alternate embodiment of a distal shim of a spacer shim instrument.
Figure 22:
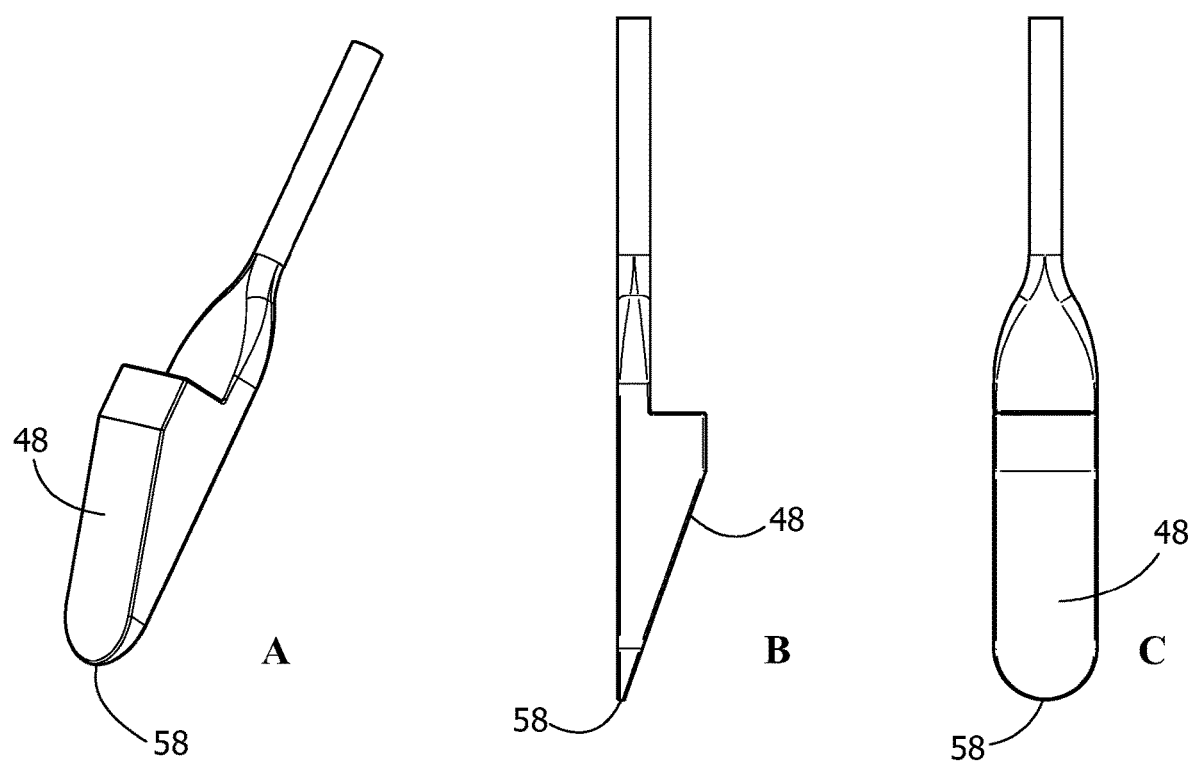
FIG. 22 A shows a front perspective view of an alternate embodiment of a distal shim of a spacer shim instrument.

In yet other embodiments, with reference now to FIG. 21 and FIG. 22, the spacer shim instrument 40 includes a distal shim portion 43 that includes a distal tip 47 that has a width that is approximately the same as the width of the distal wedge portion 54 or slightly tapered relative to the width dimension of the distal wedge portion 54. Referring now to FIG. 21, as depicted, the distal wedge portion 54 includes a distal extension 57 that tapers on its distal extension face 59 and has a distal extension edge 58 that is radiused, and a distal extension face 59 adjacent the substantially flat wedge face 48, the distal extension 57 face 59 being generally parallel to the long axis of the spacer shim instrument 40, wherein the wedge back face 56 of the distal wedge portion 54 of the distal shim portion 43 is substantially flat. And in a further alternate embodiment, referring now to FIG. 22, the spacer shim instrument 40 includes a distal shim portion 43 that includes a distal tip 47 that has a width that is approximately the same as the width of the distal wedge portion 54 or slightly tapered relative to the width of the distal wedge portion 54. As depicted in FIG. 22, the distal wedge portion 54 tapers on its wedge back face 56 and has a distal tip 47 that is radiused adjacent the substantially flat face 48. It will be appreciated in view of the various alternate embodiments shown for the distal shim portion 43, that the shim can generally taper along the length that includes the inverted wedge in one or both of its width and thickness dimensions, and can have a distal tip 47 that terminates in a shape that is one of a conical, frusto-conical, pyramidal, frusto-pyramidal, and polygonal. More generally, in addition to and encompassing the embodiments of the distal wedge portion 54 as described herein, the distal shim portion 43 may have along at least a portion of its length, including at a distal edge, a cross sectional shape selected from cylindrical, or non-cylindrical, including hemi-cylindrical, square, and hexagonal, and other polygonal shapes.

In various embodiments, the spacer shim instruments 40 may have alternate shapes, such as curvilinear cams that articulate to drive an implant to follow a sideways path away from its initial position and toward another area within the disc space. And in some embodiments, there may be an array of shims or of spacer shim instruments 40 having varying profiles selected from linear and curvilinear and having different sizes to enable selection of spacing for advancing movement of an implant advancer instrument 60 within a disc space. Thus, in some embodiments, arrays of spacer shim instruments 40 may be provided that are sized for matching the dimensions of a selection of implants, or for selection of spacing distance between the distractor blade instrument 20 and the implant advancer instrument 60, or both.

Implant Advancer Instrument

The implant advancer instrument 60 is engageable with one or both of the distractor blade instrument 20 and the spacer shim instrument 40, and is adapted with an actuator 64 at a proximal end 61. Referring again to the drawings, FIG. 7 A shows an image of a sub assembly of the spacer shim instrument 40 and implant advancer instrument 60 and components of the surgical instrument assembly 10 shown in FIG. 1.

Figure 9:
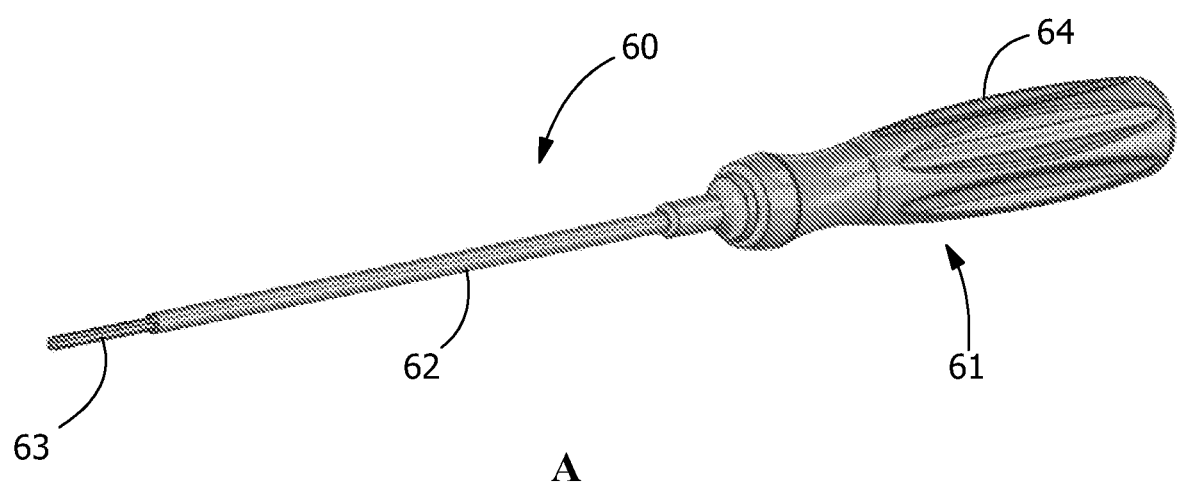
FIG. 9A shows a representative embodiment of an implant advancer instrument of the implant positioner system shown in FIG. 1.
FIG. 9B shows the distal portion of the implant advancer instrument shown in FIG. 9A, having according to the depicted embodiment a generally circular shaft, that turns into a square cross section to engage with the slot in the wedge.
Figure 9:
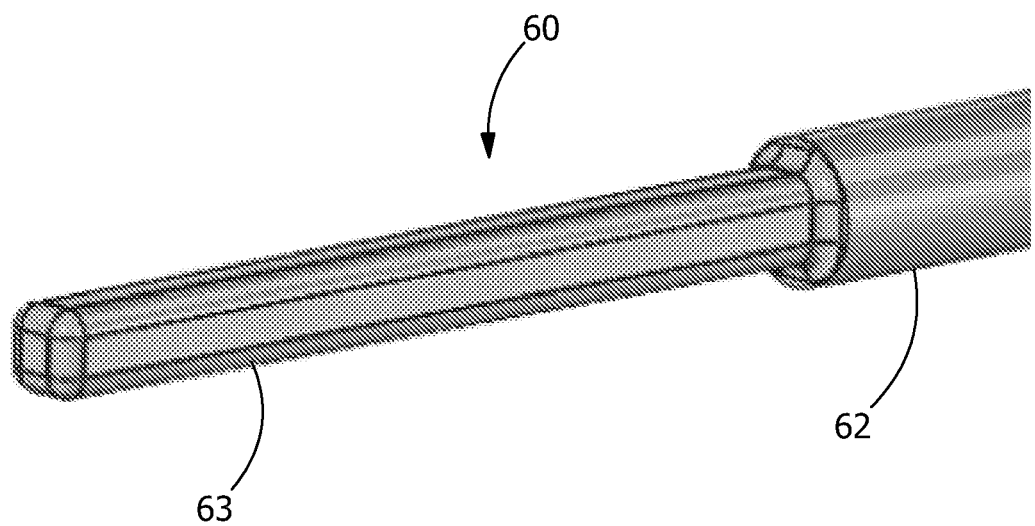

The implant advancer instrument 60 is operable between at least two modes, including as shown in FIG. 1 wherein the implant advancer instrument 60 is shown in an open configuration, and FIG. 2 which shows an image in an alternate operational mode of the surgical instrument assembly 10 shown in FIG. 1 wherein the implant advancer instrument 60 is in a closed configuration. According to the various embodiments, the implant advancer instrument 60 may have a variety of proximal end handles and actuation features. In one example, FIG. 9 A shows a representative embodiment of an implant advancer instrument 60 of the surgical instrument assembly 10 shown in FIG. 1, wherein in FIG. 9 the implant advancer instrument 60 has an elongate handle 24 at its proximal end 61 that is coaxial with its body 62. In accordance with alternate embodiments, the implant advancer instrument 60 includes at its proximal end 61 an actuator 64 comprising a pusher grip 65 that is at an angle relative to its body 62, such as shown in FIG. 1, the pusher grip 65 operating in a pivotal manner for actuating the implant advancer instrument 60 from a closed to an extended configuration, wherein the distal persuader element 63 can be moved into contact with an implant to advance its movement medially.

In various embodiments, the implant advancer instrument 60 has an body 62 and at its distal end a persuader element 63. Referring again to the drawings, FIG. 9 B shows the distal portion of the implant advancer instrument 60 shown in FIG. 9 A, the body 62 having a generally circular shaft that transitions into a square cross section (the distal persuader element 63) to engage with the slot in the spacer shim instrument 40. It will be appreciated that in other embodiments, the body, and distal and proximal portions of the instrument may vary.

In accordance with some embodiments, the implant advancer instrument 60 includes at its distal end a shaped portion adapted for insertion in the open receiving channel 49 within the flat face 48 of the wedge 46, wherein the shaped portion and the open receiving channel 49 have a cross sectional shape selected from cylindrical, or non-cylindrical, including hemi-cylindrical, square, and hexagonal, and other polygonal shapes. In use, actuation of the implant advancer instrument 60 at its proximal end 61 results in pivotal motion or levering of the distal end from a closed to an extended position to engage with an implant. In other embodiments, the implant advancer instrument 60 may be actuated by some means other than pivotal movement.

Figure 10:
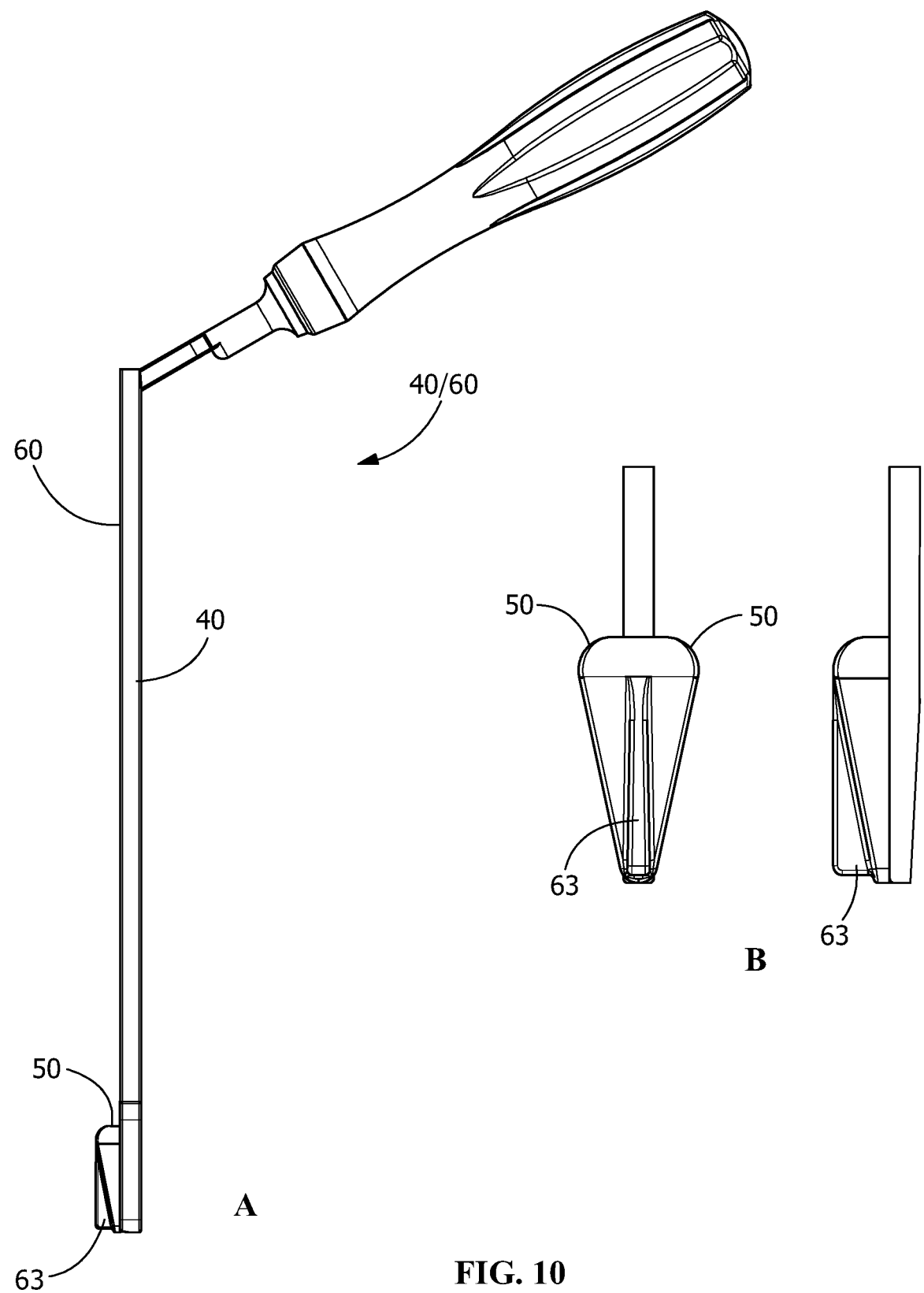
FIG. 10A shows an image of an alternate embodiment of an implant advancer instrument having a rectangular shaped pusher block at its distal end.
FIG. 10B shows the implant advancer instrument shown in FIG. 10A in the context of the distal shim portion of an embodiment of a spacer shim instrument.

And in accordance with yet other embodiments, the implant advancer instrument 60 includes at its distal end a shaped portion that is not continuous such as a cylinder or other shape, and includes a shaped extended portion, such as for example a shoulder or extension having a shape that is complimentary to that of a spacer shim instrument 40 to enhance the sideways movement of an implant advancer instrument 60 in the disc space. In accordance with the embodiments depicted in FIG. 10, the shoulder is a generally rectangular shaped extension from the tip that is guided into the spacer shim instrument 40 and oriented to exert force against the implant from a most distal point on the instrument assembly. Pivotal actuation of the implant advancer instrument 60 further enhances the lateral pressure that may be exerted on an implant to urge its sideways motion, in some embodiments medially toward the center of the disc space.

System Instrument Handles and Proximal Engagement Features

Figure 11:
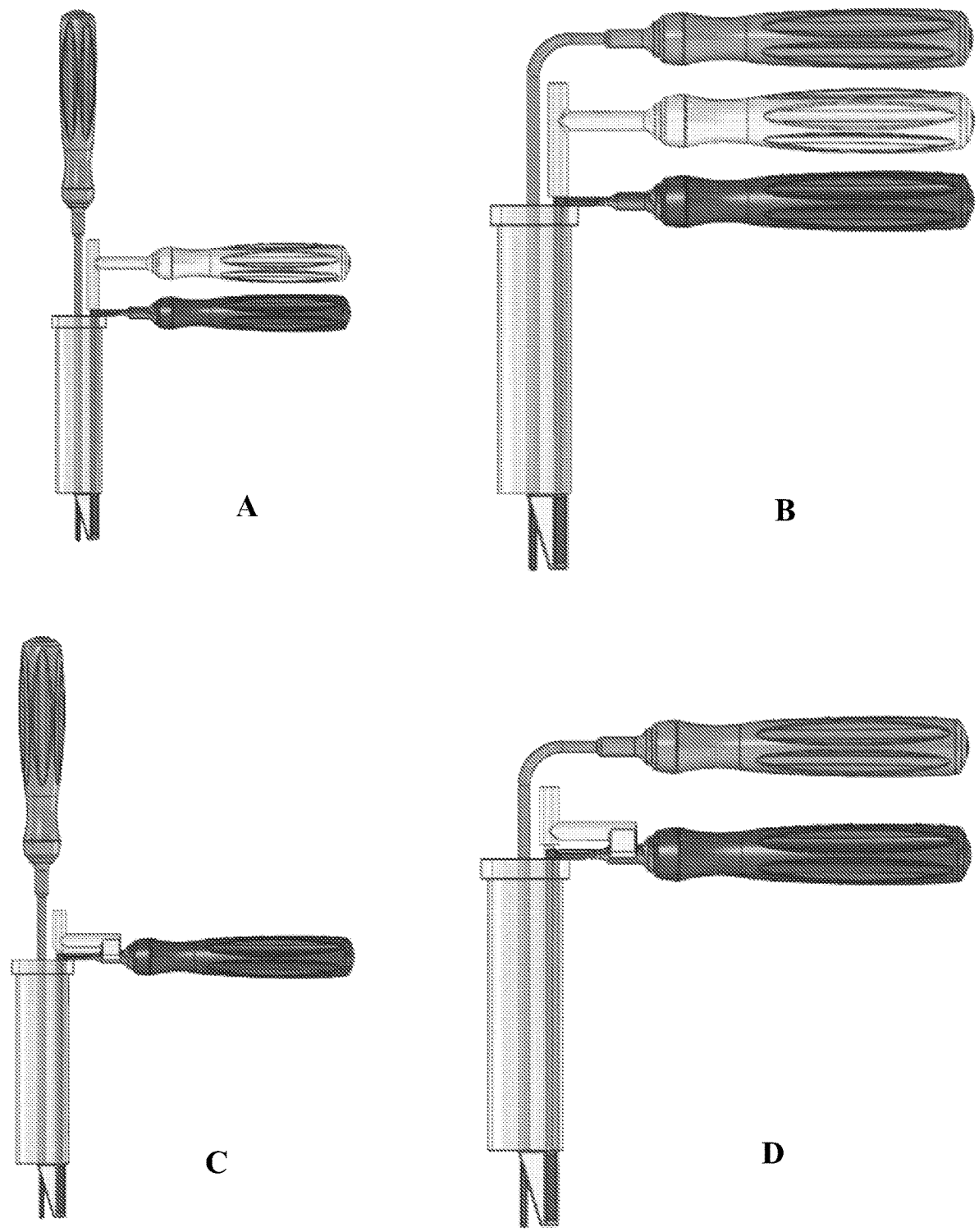
FIG. 11A shows a first embodiment of an implant positioner system with the distractor blade instrument, spacer shim instrument and implant advancer instrument assembled and represented in the context of a tissue retractor tube used for transforaminal access, wherein the implant advancer instrument is shown as having a straight handle.
FIG. 11B shows a second embodiment of an implant positioner system with the distractor blade instrument, spacer shim instrument and implant advancer instrument assembled and represented in the context of a tissue retractor tube used for transforaminal access, wherein the implant advancer instrument is shown as having a handle oriented at 90 degrees relative to the extended and distal portions of its shaft.
FIG. 11C shows a third embodiment of an implant positioner system with the distractor blade instrument, spacer shim instrument and implant advancer instrument assembled and represented in the context of a tissue retractor tube used for transforaminal access, wherein the implant advancer instrument is shown as having a straight handle, and wherein the spacer shim instrument includes a clip for fixed engagement with the distractor blade instrument (carriage)
FIG. 11D shows a fourth embodiment of an implant positioner system with the distractor blade instrument, spacer shim instrument and implant advancer instrument assembled and represented in the context of a tissue retractor tube used for transforaminal access, wherein the implant advancer instrument is shown as having a handle oriented at 90 degrees relative to the extended and distal portions of its shaft, and wherein the spacer shim instrument includes a clip for fixed engagement with the distractor blade instrument (carriage)

In accordance with the various embodiments, the system may have any of a variety of handles and actuators at their proximal ends and may comprise any of a variety of features for inter-engagement between them for assembly and actuation. FIG. 11 A shows a first embodiment of an implant positioner system with the distractor blade instrument 20, spacer shim instrument 40 and implant advancer instrument 60 assembled and represented in the context of a tissue retractor tube used for transforaminal access, wherein the implant advancer instrument 60 is shown as having a straight handle and the spacer shim instrument 40 and distractor blade instrument 20 have handles 24 oriented at 90 degrees relative to the long axis of the system. In an alternate embodiment, as shown in FIG. 11 B, an implant advancer instrument 60 positioner system includes a distractor blade instrument 20, spacer shim instrument 40 and implant advancer instrument 60 wherein the implant advancer instrument 60 all have a handle 24 oriented at 90 degrees relative to the extended and distal portions of their respective shafts along the long axis of the system. In yet another embodiment, as shown in FIG. 11 C, the implant advancer instrument 60 has a straight handle 24, and the spacer shim instrument 40 includes a clip 44 for fixed engagement with the distractor blade instrument 20 which engagement is secondary to its engagement with the distractor blade instrument 20 carriage, and the distractor blade instrument 20 has a handle 24 oriented at 90 degrees. And in yet another embodiment, as shown in FIG. 11 D, each of the distractor blade instrument 20 and the implant advancer instrument 60 has a handle 24 oriented at 90 degrees relative to the extended and distal portions of its shaft, and the spacer shim instrument 40 includes a clip 44 for fixed engagement with the distractor blade instrument 20.

Thus, in accordance with the various embodiments, a system for performing spinal interbody fusion surgery includes a system for manipulating and positionally adjusting one or more interbody implants within a disc space, the system having a proximal end comprising grasping and manipulating features, and a distal end comprising interbody implant manipulation instruments that are actuated by the grasping and manipulating features and are insertable into a surgical field within the spine.

The interbody implant instruments include an elongate distractor blade instrument 20 having a blade-shaped endplate distractor having an elongate engagement feature along a length between the proximal and distal ends, a spacer shim instrument 40 having an body 22 adapted for slidable contact with the engagement feature of the endplate distractor blade instrument 20 and having at its distal end a distal shim portion 43 for contacting and pushing against an interbody implant, and an implant advancer instrument 60 that articulates adjacent the distal spacer shim instrument 40 between a closed configuration and an extended configuration to contact an interbody implant.

In use, the spacer shim instrument 40 is adapted to be slidably directed in a distal direction to be in contact with and between the endplate distractor instrument 20 and an interbody implant positioned between endplates in a disc space, whereby the distally directed slidable motion of the spacer shim instrument 40 exerts at least a sideways force on the interbody implant advancer instrument 60 to direct one or more of sideways and rotational translation of the interbody implant advancer instrument 60 within the disc space. The implant advancer instrument 60 is adapted to be actuated from its closed to its extended configuration and into contact with an interbody implant advancer instrument 60 that is adjacent the spacer shim instrument 40, whereby the extension of the implant advancer instrument 60 exerts a force on a contacted interbody implant to achieve one or more of sideways and rotational translation of one or more adjacent interbody implant advancer instruments 60 into the disc space.

Arrays

In accordance with some embodiments, the instrument system is selected from arrays of each of the instruments provided in varying dimensional aspects, including size and shape of the distal shim portion 43 of the spacer shim instrument 40, width and length and contour of the distal blade 23 of the distractor blade instrument 20, and shape and length of the implant advancer instrument 60, the features selected to accommodate varying dimensions of access channels and for controlling direction and extent of movement of interbody devices within the disc space.

In accordance with some embodiments, one or more of the distractor blade instrument 20, the spacer shim instrument 40, and the implant advancer instrument 60 is selected from at least one instrument array comprising a plurality of instruments wherein each instrument in the array varies from each of the other instruments in the array in at least one aspect. According to some such embodiments, the at least one instrument array is selected from: an array of distractor blade instruments 20 provided in varying dimensional aspects, including width and length and contour of the distal blade 23 of the distractor blade instrument 20; an array of spacer shim instruments 40 including variations in size and shape of the distal shim portion 43 of the spacer shim instrument 40; and in some embodiments including an implant advancer instrument 60, an array of implant advancer instruments 60. In accordance with the various embodiments, the features of each of the instruments is selected from the arrays to accommodate varying dimensions of access channels and for controlling direction and extent of movement of interbody devices within the disc space.

Kits

It will be appreciated that in some embodiments, surgical kits are provided that include an instrument system comprising at least one or more of a distractor blade instrument 20, a spacer shim instrument 40, an implant advancer instrument 60, a tissue retractor tube 80 or tube insert adapted with a plurality of slots 81 and a plurality of tabbed clips 82, one or more of insertable elongate instruments for irrigation, lighting, visualization, neuromonitoring, the kits provided based on one or more of size features of a patient or a patient anatomy.

System in the Context of a Representative TLIF Retractor Tube

Figure 12:
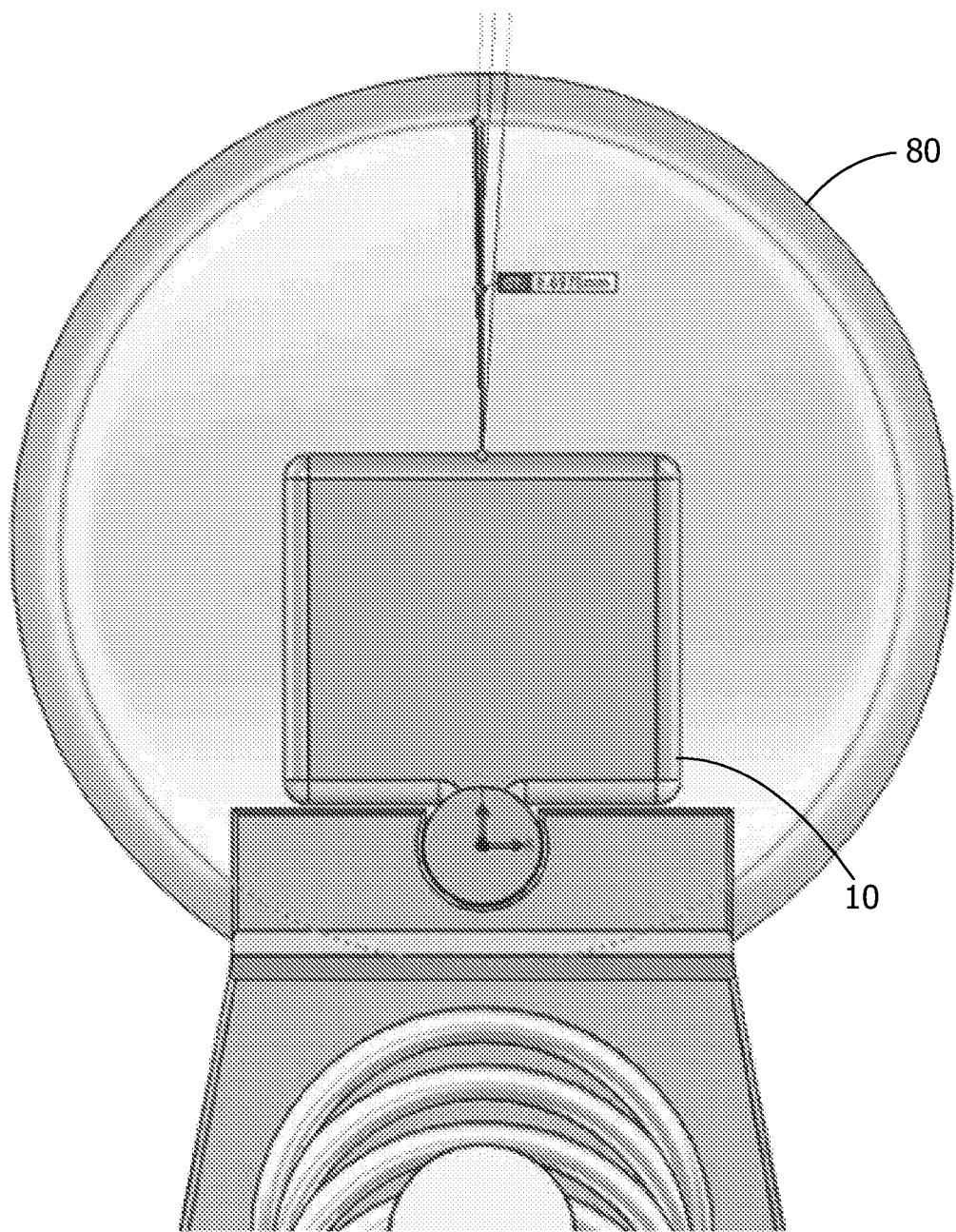
FIG. 12 shows a view of the assembled implant positioner system along the long axis of its length dimension and represented in the context of a tissue retractor tube used for transforaminal access.
Figure 13:
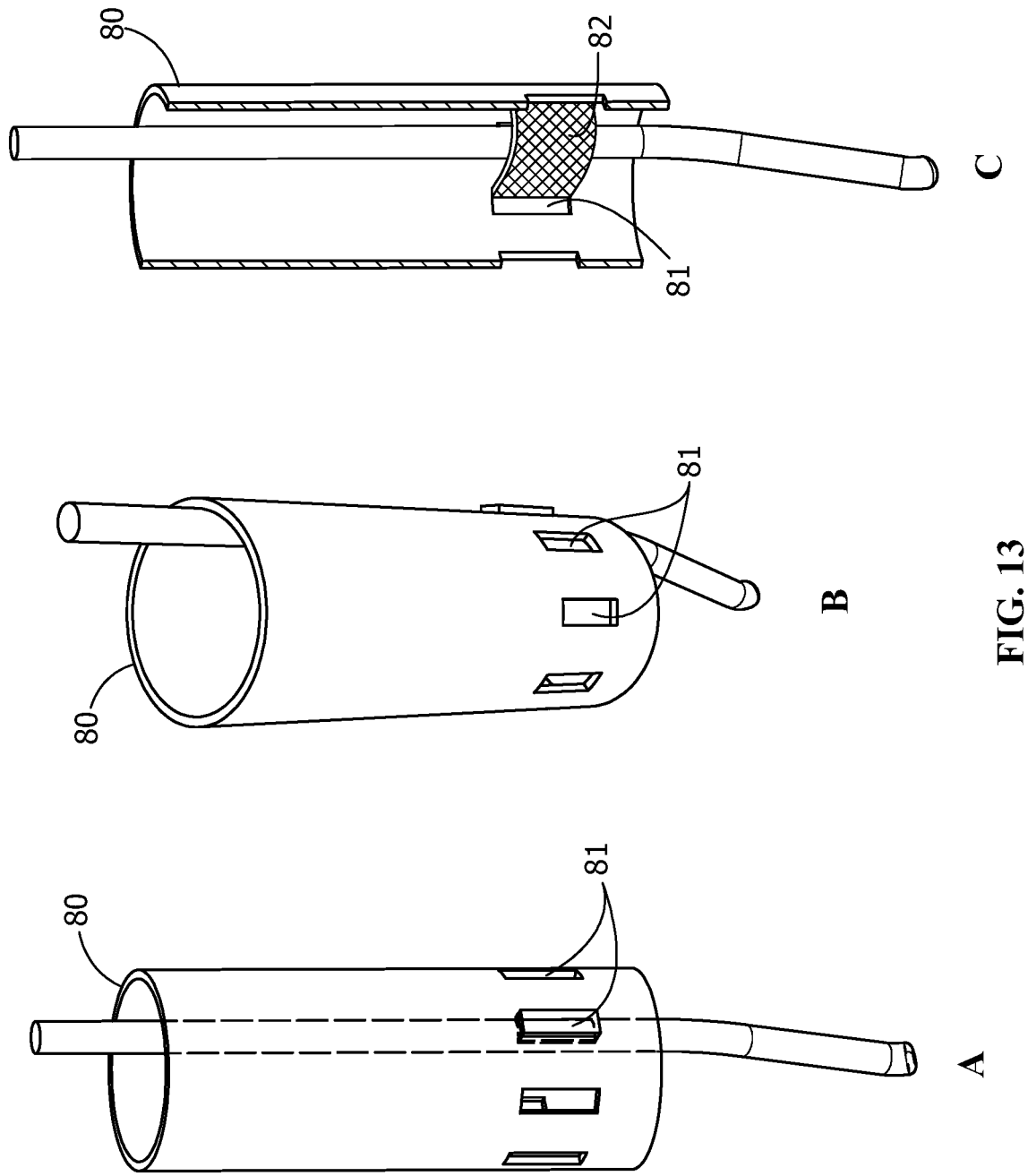
FIG. 13 A, FIG. 13 B and FIG. 13 C each shows an alternate view of an embodiment of a retractor tube adaptation for securing one or a variety of instruments to a retractor to provide one or more of suction, irrigation, and neuro-monitoring by attachment to the wall of the retractor tube using a clip to capture the inserted instrument and secure it via tabs inserted into slots on the tube wall.
Figure 14:
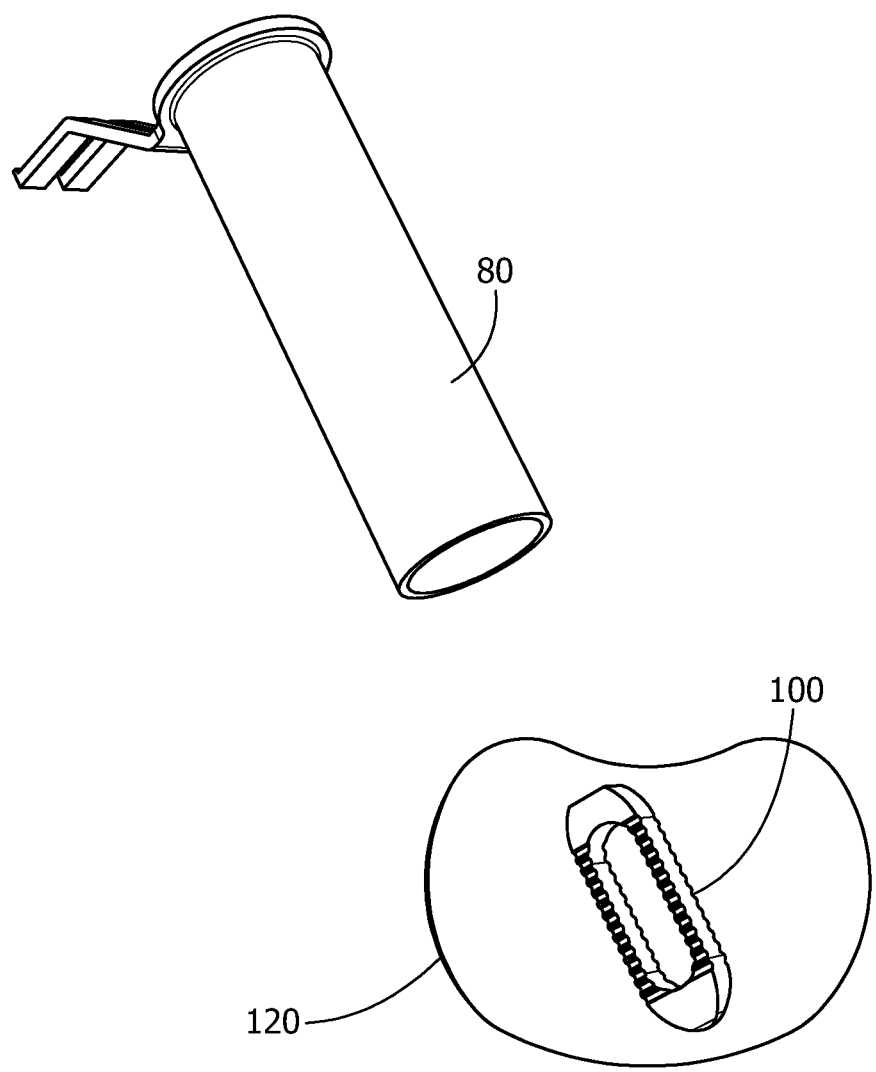
FIG. 14 shows an image of a retractor tube in relation to a drawn representation of an intervertebral space with a first implant positioned thereon.
Figure 15:
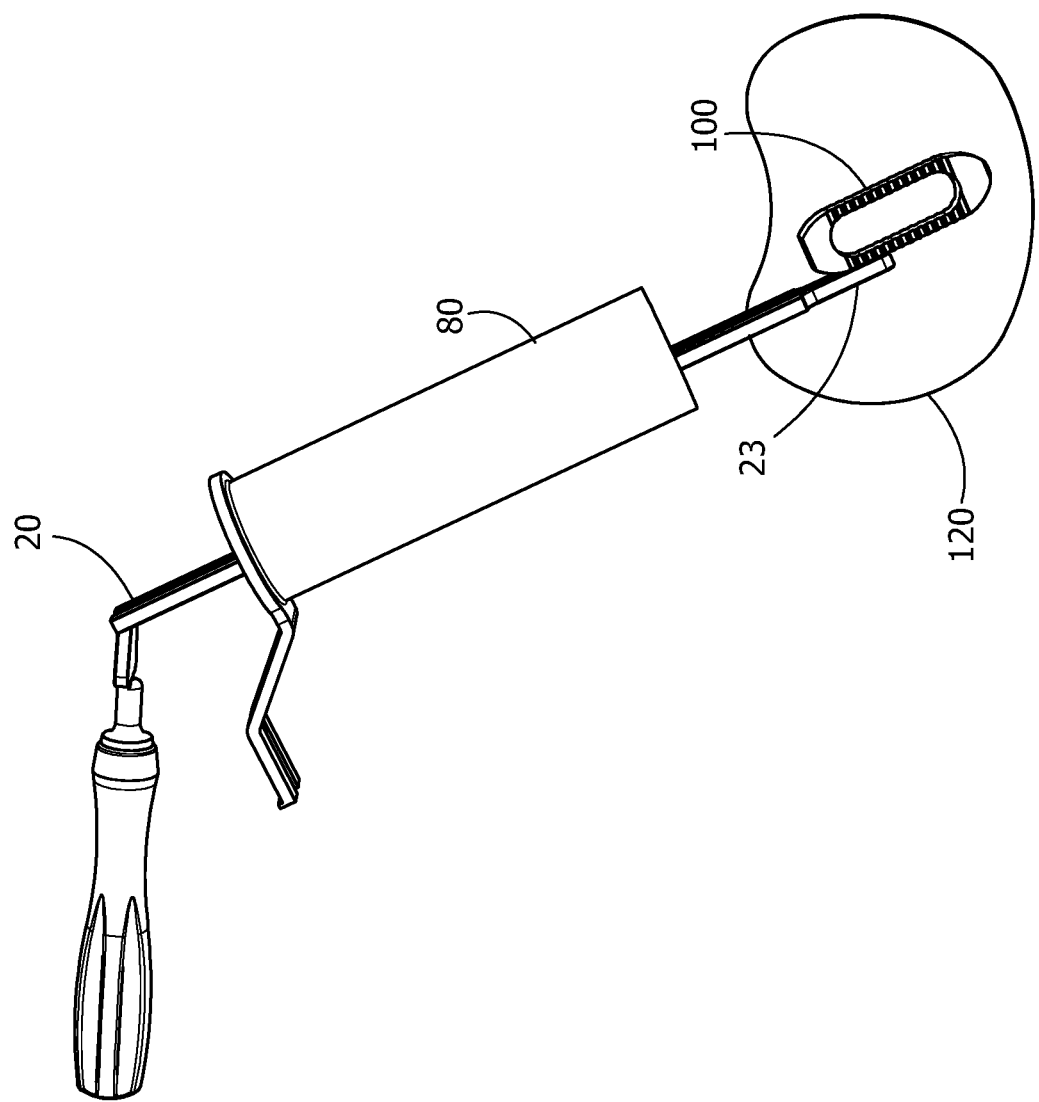
FIG. 15 shows an image of a sub assembly in relation to a drawn representation of an intervertebral space with a first implant positioned thereon, the sub assembly including a retractor tube and a distractor blade instrument inserted there through with its distal end positioned adjacent to the implant as it would be in situ in a surgical setting.
Figure 16:
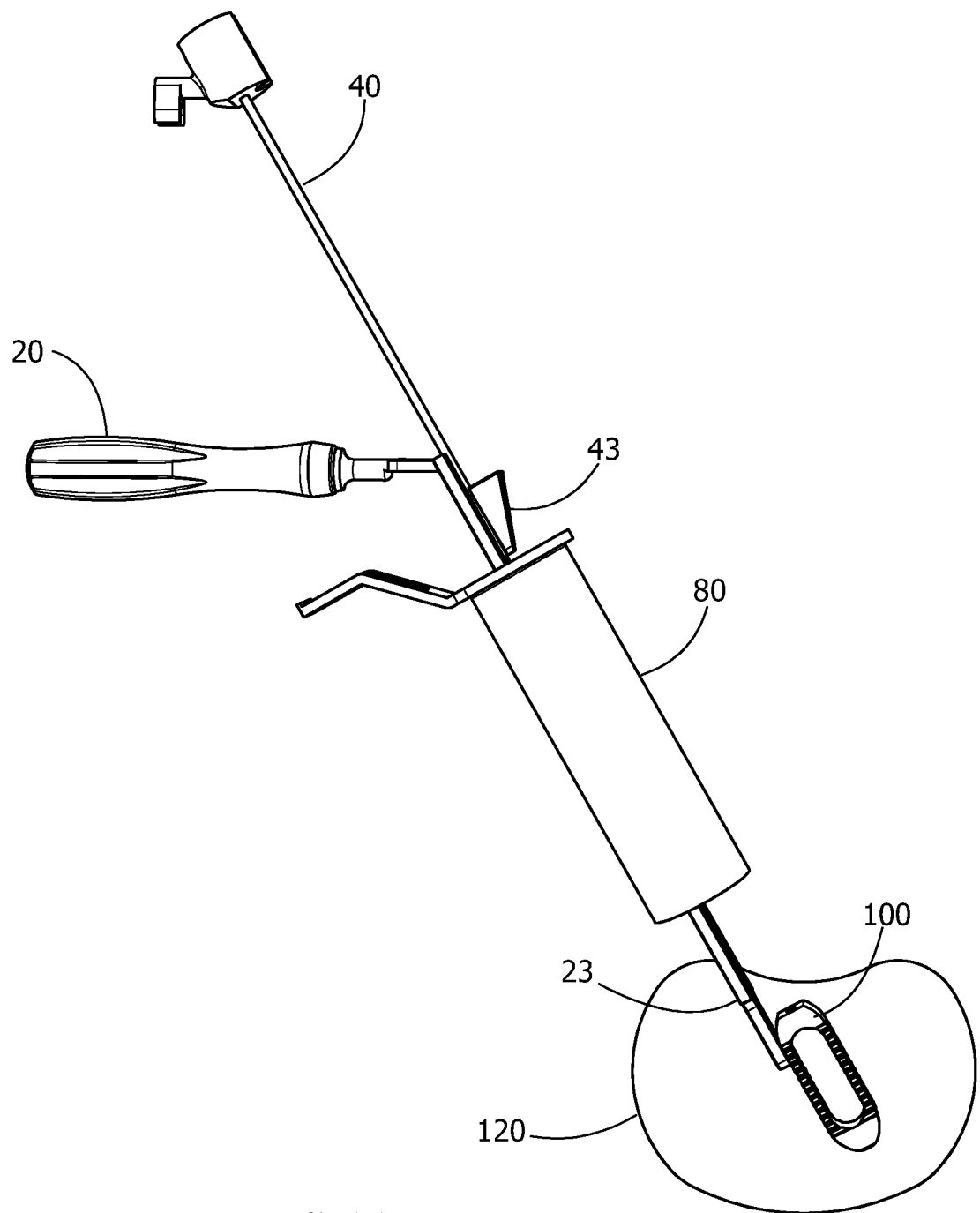
FIG. 16 shows an image of a sub assembly as shown in FIG. 15, the sub assembly further including a spacer shim instrument inserted at its distal end with the carriage of the distractor blade instrument, the shaft of the spacer shim instrument inserted into the channel therein.
Figure 17:
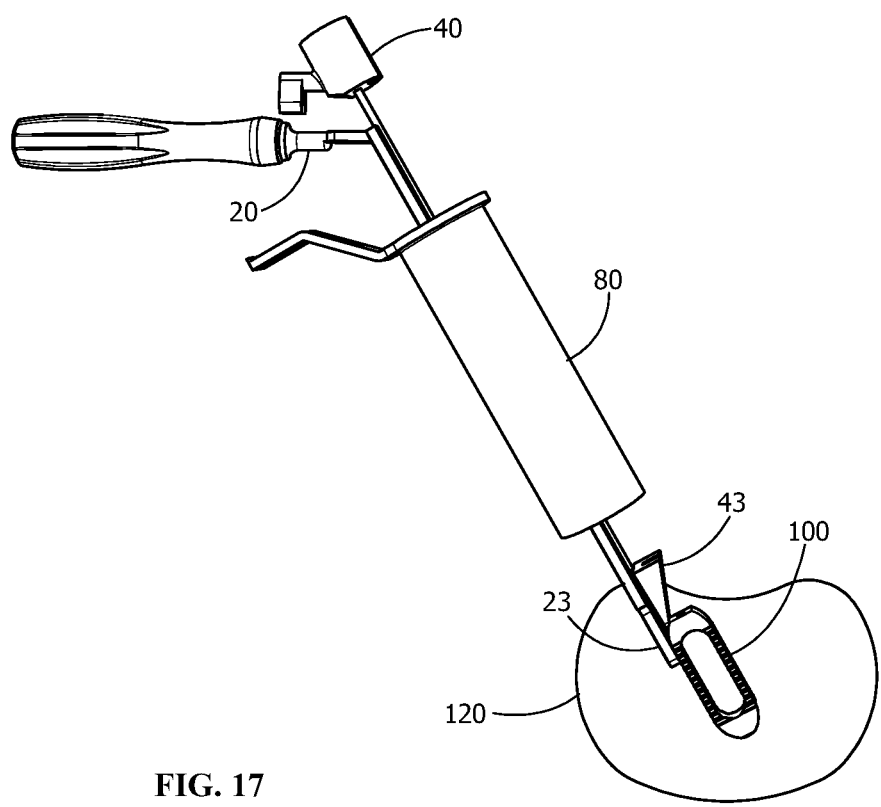
FIG. 17 shows an image of a sub assembly as shown in FIG. 15, the spacer shim instrument shown advanced further along the length of the distractor blade instrument and just proximal to the upper end of the implant.
Figure 18:
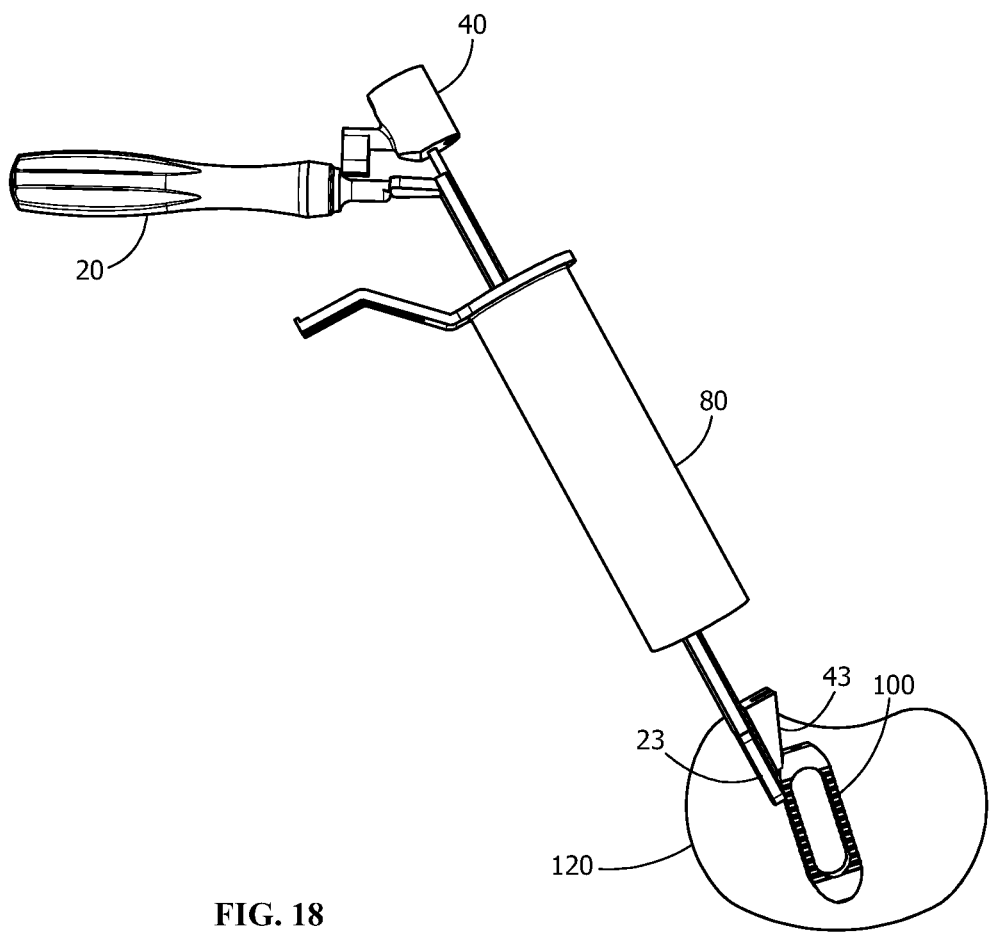
FIG. 18 shows an image of a sub assembly as shown in FIG. 15, the spacer shim instrument shown advanced further along the length of the distractor blade instrument and contacting the side of the implant and persuading it in the direction of the contralateral annulus.
Figure 19:
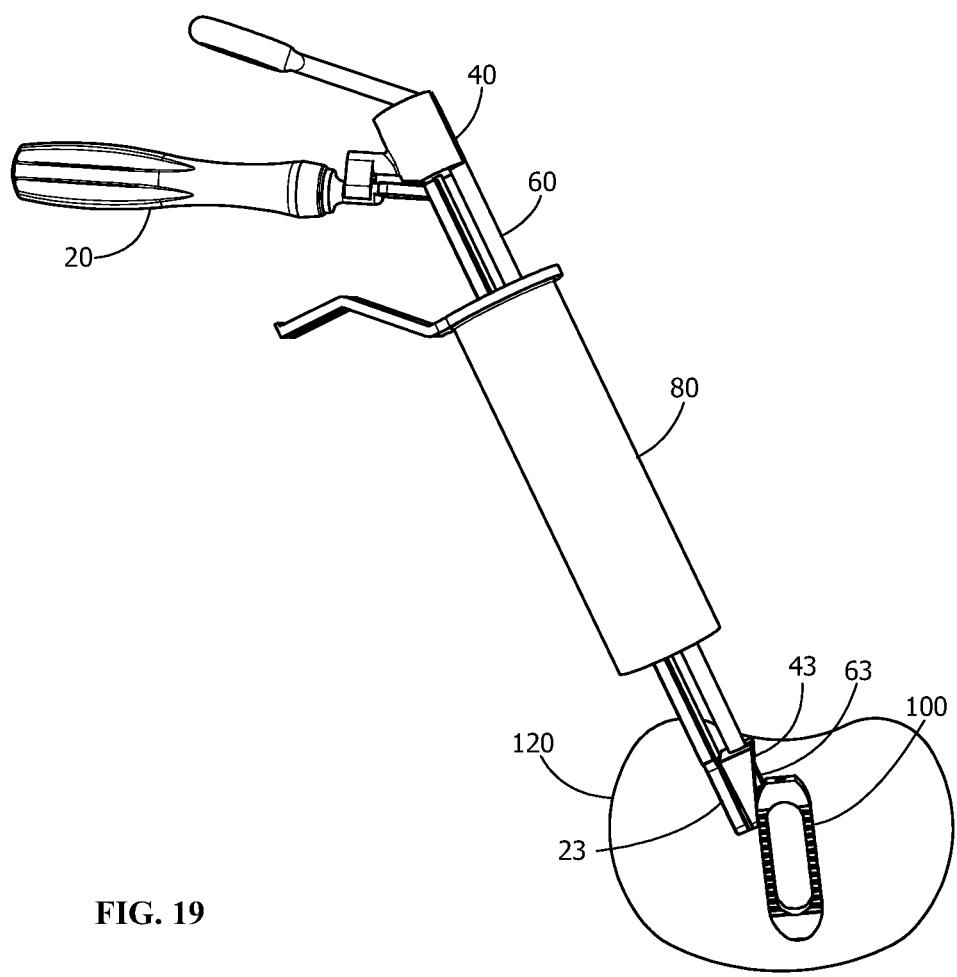
FIG. 19 shows an image of a sub assembly as shown in FIG. 15, the spacer shim instrument shown advanced into locked engagement at its proximal end with the distractor blade instrument and at its full contact with the implant, and further including an implant advancer instrument inserted at its distal end into and through the channel of the spacer shim instrument and levered away from the spacer shim instrument into contact with the implant to further urge it toward the contralateral annulus.

Referring now to FIG. 12, a view of the assembled surgical implant assembly 10 is shown along its length dimension 31 and represented in the context of a tissue retractor tube 80 used for transforaminal access; a view of the instruments of the system described herein are shown as inserted through a tissue retractor tube 80 (typically 22 mm tube) such that there is roughly 18 mm from the flat on the anterior to posterior positioned blade to the farthest point on the inner diameter of the tube. In view of the fact that most implants have a generally square cross section and are overall rectangular in shape, either straight or curved, the space constraints in a standard tube involve fitting what is essentially a square cage through a round tube, thus the clearance space for insertion of a cage in the space not occupied by the instrument system hereof can be limiting in terms of the selected implant size. As shown in the schematic of FIG. 12, use of the instant system where the spacer shim instrument 40 has a width dimension 30 of about 9 to 10 mm, there is approximately 8.5 mm of space remaining for insertion of the implant if the instrument system is in place prior to initial or subsequent implant insertion. Of course, it will be appreciated, that in accordance with some surgical approaches, the spacer shim instrument 40 and other components may be deployed into the disc space after insertion of an implant and may be removed prior to insertion of subsequent implants. And in yet other embodiments, the size and contour of a spacer shim instrument 40 may be selected to allow placement of both the instrument system and the implant simultaneously.

In some embodiments, the surgical techniques hereof can benefit from use of one or more insertable instruments. In some examples these would include irrigation, suction, electro/neuromonitoring, fiber optic lighting, camera or other instruments to facilitate the surgical procedure. Provided herein are adaptations for retractor tubes to facilitate the securement of such instruments within the tube. In some embodiments, the adaptations include one or more flexible clips that are adapted to be secured to the walls of the tube. As depicted, the clips are flat ribbon shaped strips that are semi rigid and have tabs at their ends for engagement into slots on the wall of the tube. In use, the instrument, such as a tubular light, camera, neuro-monitoring cable, or the like is inserted in the tube into the surgical field, and is clipped to the tube by engagement of the clip tabs in the slots. As depicted, the tube is adapted with a circumferential ring of slots allowing flexibility in the position of placement of the instrument. It will be appreciated that the shape of the slots may be varied, as well as their distribution and orientation around the circumference, as well as their proximal to distal positioning. And it will be appreciated that in various embodiments, the tubes may be adapted with slots at more than one position along the length from the proximal to distal ends of the tubes, and that the shapes, sizes, number and distribution of the slots may vary to accommodate varying sized clips and to support instruments along a greater portion of the length of the tube.

Surgical Technique

Also in accordance with the disclosure is a surgical technique for performing a procedure on the spine of a patient utilizing the surgical instruments and system hereof to enable controlled and reliable delivery of two or more implants into the intervertebral space without expulsion, which in the case of a procedure such as TLIF, the movement is along a substantially lateral to medial path of travel between the end plates.

Provided herein are methods for performing spinal interbody implant fusion surgery, in some examples a posterior or transforaminal access surgery. The methods include the steps, either in the provided order, or alternately in another order consistent with the disclosure, including the following after initial placement of an interbody implant (or other device) in the disc space. Directing an elongate distractor blade instrument 20 into a spinal disc space and between adjacent endplates, a distal blade 23 of the distractor blade instrument 20 adjacent and at least partially contacting an interbody implant within the disc space, then slidably advancing a spacer shim instrument 40 along the elongate blade in a distal direction and into contact with a proximal end of the interbody implant. Advancing the spacer shim instrument 40 distally between the distractor blade instrument 20 and the interbody implant, whereby the distally directed motion of the distal shim portion 43 of the spacer shim instrument 40 exerts at least a sideways force on the interbody implant to direct one or more of sideways and rotational translation of the interbody implant within the disc space. Actuating an implant advancer instrument 60 that is adjacent the spacer shim instrument 40 from a closed (see for example, FIG. 2) to an extended configuration (see FIG. 1) and into contact with the interbody implant that is adjacent the distal shim portion 43 of the spacer shim instrument 40, whereby the extension of the implant advancer instrument 60 exerts a force on the contacted interbody implant to achieve one or more of sideways and rotational translation of at least the adjacent interbody implant into the disc space.

Upon achieving desired positioning or repositioning of the implant, withdrawing one or more of the elongate blade, spacer shim instrument 40 and implant advancer instrument 60. Optionally, inserting another interbody implant into the disc space. Optionally, repeating the foregoing steps one or more times.

Figure 20:
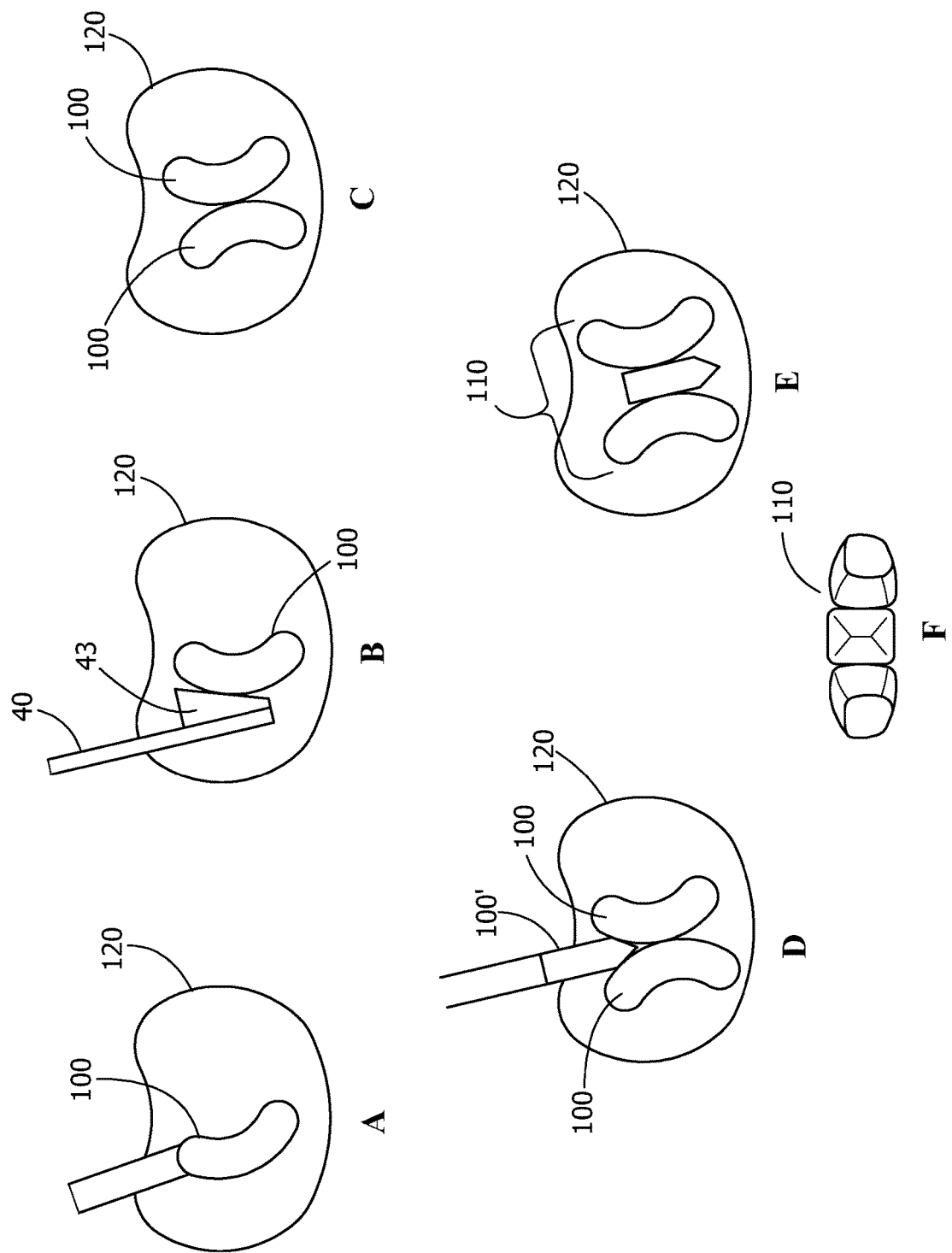
FIG. 20 A, FIG. 20 B, FIG. 20 C, FIG. 20 D, FIG. 20 E, and FIG. 20 F each show sequential steps in a scheme for insertion, arrangement and orienting three implant assembly components using a spacer shim instrument according to the disclosure.

Referring to the drawings, FIG. 14-FIG. 19 show in successive views images of a tissue retractor tube 80 in relation to a drawn representation of an intervertebral space with a first implant positioned thereon; and sub-assemblies and full assemblies according to the disclosure to simulate translation of an implant using the instruments and methods hereof. In yet another embodiment, FIG. 20 shows a scheme for insertion, arrangement and orienting three implant assembly components using a spacer shim instrument 40 according to the disclosure. The depicted scheme enables the surgeon to create in situ an implant assembly that is optimized to cover a large portion of the endplates while benefitting from the less invasive TLIF approach, whereby two curved shaped implant advancer instrument 60 components are inserted in sequence and spaced apart using at least the spacer shim instrument 40, then a third implant advancer instrument 60, which is depicted as a straight bulleted implant, is passed along the path between the first two implants to push the medial implant in a medial direction. In a typical surgical setting where, the lateral annulus is retained intact, it is contemplated that the more lateral implant will be less likely to move laterally as compared to the travel of the medical implant towards the center of the disc space. Of course, in the event that the lateral annulus is not intact it would be possible to use the distractor blade instrument 20 to buttress the lateral implant and minimize its lateral travel when the third implant is inserted.

Of course, it will be understood that the schemes shown in FIG. 20 and in FIG. 14-FIG. 19 are not limited in terms of the number or arrangement of implants or the use of one or more of the distractor blade instrument 20, spacer shim instrument 40 and implant advancer instruments 60. The appropriate combinations are selected by the surgeon based upon the surgeon's consideration of one or more of the following: the clinical circumstances, the needed implant sizes, and desired configuration and placement of the implants.

While the disclosed embodiments have been described and depicted in the drawings in the context of the human spine, it should be understood by one of ordinary skill that all or various aspects of the embodiments hereof may be used in connection with other species and within any species on other parts of the body where deep access within the tissue is desirable.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts and features into additional embodiments and uses within the scope of the general inventive concepts, even if such embodiments are not expressly disclosed herein. Additionally, even though some features, concepts and aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated.

Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

The invention claimed is:

1. A system for performing spinal surgery, comprising:
an assembly comprising one or more manipulation instruments for manipulating and positionally adjusting one or more implants within a spinal disc space, the assembly having a proximal end comprising one or more of grasping and manipulating features, and a distal end comprising one or more manipulation features that are actuated by the one or more grasping and manipulating features, the assembly comprising
a shim instrument comprising
a body between proximal and distal ends, at a distal end of the body a generally wedge shaped spacer shim in an inverted orientation, the spacer shim comprising a base portion that is oriented proximally, and a wedge portion that is oriented distally, the wedge portion comprising a distal tip, and at least one substantially flat face along at least the wedge portion of the spacer shim, the substantially flat face oriented at an angle relative to a long axis of the shim instrument body.

2. A system for performing spinal surgery according to claim 1, the generally wedge shaped spacer shim comprising at least one of:
   a distal extension from the wedge portion, the distal extension having a substantially flat face that is oriented generally parallel relative to the long axis of the shim instrument body, and
   on the base portion a substantially flat face that is oriented generally parallel relative to the long axis of the shim instrument body.

3. A system for performing spinal surgery according to claim 1, the wedge portion of the spacer shim at the distal tip having a wedge shape selected from frusto trapezoidal, frusto conical, and frusto pyramidal, and the base portion of the spacer shim having a block shape.

4. A system for performing spinal surgery according to claim 1, the body having a cross sectional shape that is selected from cylindrical, hemi-cylindrical, and polygonal.

5. A system for performing spinal surgery according to claim 1, the spacer shim at the distal end of the shim instrument having a generally triangular wedge shape, the base comprising squared proximal shoulders, the shim tapering to a tip that is a squared frusto-pyramid.

6. A system for performing spinal surgery according to claim 1, the base portion of the spacer shim comprising rounded proximal shoulders.

7. A system for performing spinal surgery according to claim 1, the base portion of the spacer shim comprising squared proximal shoulders.

8. A system for performing spinal surgery according to claim 2, wherein each of the wedge portion and one or more of a distal extension and the base portion have a width that is the same along their lengths from the proximal base to the distal tip, wherein the distal tip is radiused.

9. The system for performing spinal surgery according to claim 1, wherein the shim instrument is adapted for engagement with at least one of:
   a distractor blade instrument comprising a body between proximal and distal ends, a handle at the proximal end and a distractor blade at the distal end, and an engagement carriage along a length between the proximal and distal ends for engaging with the shim instrument, and
   an advancer instrument comprising an actuator at a proximal end and comprising at a distal end a persuader element for engaging with the shim instrument.

10. The system for performing spinal surgery according to claim 9, comprising an advancer instrument, the wedge shaped spacer shim comprising on at least one substantially flat face an open channel shaped to accommodate a distal portion of the implant advancer, the advancer instrument actuatable between a closed configuration wherein the persuader element is at least partially recessed within the open channel, and an extended configuration wherein the persuader element is at least partially extended away from the shim.

11. A system for performing spinal surgery according to claim 10, wherein each of the persuader element and the open channel has a complimentary shape, each having a cross sectional shape that is selected from cylindrical, hemi-cylindrical, and polygonal.

12. The system for performing spinal surgery according to claim 10, comprising a distractor blade instrument wherein the carriage of the distractor blade instrument comprises an elongate slot along at least a portion of its length between the proximal and distal ends and comprises at its distal end a stop feature for halting distal advancement of a spacer shim engaged with the carriage, wherein one or both the body of the spacer shim instrument and a shaped portion of the back face of the shim has a shape that is complimentary with the carriage slot of the distractor blade instrument.

13. A system for performing spinal surgery according to claim 12, wherein each of the carriage slot and the one or both the body of the spacer shim instrument and a shaped portion of the back face of the shim has a complimentary cross sectional shape that is selected from cylindrical, hemi-cylindrical, and polygonal.

14. A system for performing spinal surgery according to claim 13, wherein the distal blade has a contour that is defined by each of a width dimension, a length dimension, and a thickness dimension, the contour being one of planar and shaped.

15. A system for performing spinal surgery according to claim 14, wherein the distal blade has a shaped contour and is in at least one of its width and thickness dimensions one of angled and radiused (curved), the distal blade comprising a distal edge having corners that are one angled and radiused.

16. A system for performing spinal surgery, comprising:
   an assembly comprising one or more manipulation instruments for manipulating and positionally adjusting one or more implants within a spinal disc space, the assembly having a proximal end comprising one or more of grasping and manipulating features, and a distal end comprising one or more manipulation features that are actuated by the one or more grasping and manipulating features, the assembly comprising
   a shim instrument comprising
      a body between proximal and distal ends, at a distal end of the body a generally wedge shaped spacer shim in an inverted orientation, the wedge shaped spacer shim comprising a base portion that is oriented proximally, and a distally oriented wedge portion comprising a distal tip, and at least one substantially flat face along at least a portion of the wedge shaped spacer shim, wherein a substantially flat face is disposed on the wedge portion of the spacer shim, the substantially flat face oriented at an angle relative to a long axis of the shim instrument body and the base portion of the spacer shim comprising a substantially flat face oriented at parallel relative to a long axis of the shim instrument body, the base comprising squared proximal shoulders, the shim tapering to a tip that is a squared frusto-pyramid; and
   a distractor blade instrument comprising a body between proximal and distal ends, a handle at the proximal end and a distractor blade at the distal end, and an engagement carriage along a length between the proximal and distal ends for engaging with the shim instrument, wherein the distal blade has a back side that has an angled taper to its thickness dimension the taper originating on the back side at a proximal position along the length dimension, and the distal blade also has an angled taper to its width dimension, the taper originating on each of lateral edges at a proximal position along the length dimension, the distal blade having a cross sectional shape that is generally trapezoidal,
   wherein the carriage of the distractor blade instrument comprises an elongate slot along at least a portion of its length between the proximal and distal ends and comprises at its distal end a stop feature for halting distal advancement of a spacer shim engaged with the carriage, wherein one or both the body of the spacer shim instrument and a shaped portion of the back face of the shim has a shape that is complimentary with the carriage slot of the distractor blade instrument.

17. A system for performing spinal surgery, comprising:
an assembly comprising one or more manipulation instruments for manipulating and positionally adjusting one or more implants within a spinal disc space, the assembly having a proximal end comprising one or more of grasping and manipulating features, and a distal end comprising one or more manipulation features that are actuated by the one or more grasping and manipulating features, the assembly comprising
a shim instrument comprising
  a body between proximal and distal ends, at a distal end of the body a generally wedge shaped spacer shim in an inverted orientation, the wedge shaped spacer shim comprising a base portion that is oriented proximally, and a distally oriented wedge portion comprising a distal tip, and at least one substantially flat face along at least a portion of the wedge shaped spacer shim, wherein a substantially flat face is disposed on the wedge portion of the spacer shim, the substantially flat face oriented at an angle relative to a long axis of the shim instrument body and the base portion of the spacer shim comprising a substantially flat face oriented at parallel relative to a long axis of the shim instrument body, the base comprising squared proximal shoulders, the shim having a distal tip that is one of (i) radiused with a width dimension that is the same as a width dimension of the wedge, and (ii) tapering to a tip that is one of conical, trapezoidal, and squared frusto-pyramidal.

18. A method for performing spinal interbody fusion surgery, comprising the steps:
(i) directing a spacer shim instrument according to claim 1 into a spinal disc space and between adjacent endplates and at least partially contacting an interbody implant within the disc space;
(ii) further advancing distally the spacer shim of the spacer shim instrument, whereby the distally directed motion of the spacer shim exerts at least a sideways force on the interbody implant to direct one or more of sideways and rotational translation of the interbody implant within the disc space;
(iii) optionally, at least partially withdrawing the spacer shim from the disc space;
(iv) inserting another interbody implant into the disc space;
(v) optionally, repeating the steps (i)-(iv), one or more times.

19. A method for performing spinal interbody fusion surgery according to claim 18, further comprising the steps of
(vi) inserting into engagement with the spacer shim instrument an elongate implant advancer having a proximal end, and a distal end, and having at its distal end a distal persuader element that is engageable with a channel in the generally wedge shaped spacer shim, and
(vii) actuating the implant advancer to extend away from the spacer shim to exert at least a sideways force on the interbody implant to direct one or more of sideways and rotational translation of the interbody implant within the disc space.

* * * * *